US010875024B2

(12) United States Patent
Li et al.

(10) Patent No.: US 10,875,024 B2
(45) Date of Patent: Dec. 29, 2020

(54) METHODS AND COMPOSITIONS FOR PAPER-BASED AND HYBRID MICROFLUIDIC DEVICES INTEGRATED WITH NUCLEIC ACID AMPLIFICATION FOR DISEASE DIAGNOSIS

(71) Applicants: Xiujun Li, El Paso, TX (US); Maowei Dou, El Paso, TX (US); Delfina Dominguez, El Paso, TX (US)

(72) Inventors: Xiujun Li, El Paso, TX (US); Maowei Dou, El Paso, TX (US); Delfina Dominguez, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 868 days.

(21) Appl. No.: 14/796,127

(22) Filed: Jul. 10, 2015

(65) Prior Publication Data
US 2016/0008809 A1    Jan. 14, 2016

Related U.S. Application Data

(60) Provisional application No. 62/022,879, filed on Jul. 10, 2014.

(51) Int. Cl.
| | |
|---|---|
| *C40B 60/00* | (2006.01) |
| *B01L 3/00* | (2006.01) |
| *C12Q 1/6865* | (2018.01) |
| *C12Q 1/6867* | (2018.01) |
| *C12Q 1/689* | (2018.01) |
| *C12Q 1/68* | (2018.01) |
| *B01L 7/00* | (2006.01) |

(52) U.S. Cl.
CPC ......... *B01L 3/50851* (2013.01); *B01L 3/5027* (2013.01); *B01L 3/502715* (2013.01); *C12Q 1/689* (2013.01); *C12Q 1/6865* (2013.01); *C12Q 1/6867* (2013.01); *B01L 7/52* (2013.01); *B01L 2200/0605* (2013.01); *B01L 2300/0636* (2013.01); *B01L 2300/0681* (2013.01); *B01L 2300/0816* (2013.01); *B01L 2300/0864* (2013.01); *B01L 2300/0867* (2013.01); *B01L 2300/0887* (2013.01); *B01L 2300/0893* (2013.01); *B01L 2300/126* (2013.01)

(58) Field of Classification Search
CPC .................... C12Q 1/67; B01L 3/00
See application file for complete search history.

(56) References Cited

U.S. PATENT DOCUMENTS

| | | | | |
|---|---|---|---|---|
| 7,404,932 | B2 * | 7/2008 | Chen .................. | B01J 20/205 422/535 |
| 8,546,752 | B2 * | 10/2013 | Henion ................ | G01N 1/405 250/282 |
| 2005/0208539 | A1 * | 9/2005 | Vann ................. | B01L 3/502707 435/6.11 |
| 2010/0021910 | A1 * | 1/2010 | Cao .................. | B01L 3/502753 435/6.11 |

FOREIGN PATENT DOCUMENTS

WO      WO-9639813 A1 * 12/1996  ....... C12Q 2527/125

OTHER PUBLICATIONS

Zuo et al., A PDMS/Paper/Glass Hybrid Microfluidic Biochip Integrated With Aptamer-Functionalized Graphene Oxide Nano-Biosensors for One-Step Multiplexed Pathogen Detection, Lab on a Chip, 2013, 13, 3921-3928. (Year: 2013).*
Li et al., A PDMS/Paper Hybrid Microfluidic Device Integrated With Graphene Oxide-Based Nano-Biosensors for Multiplexed Pathogen Detection, 17th International Conference on Miniaturized Systems for Chemistry and Life Sciences (MicroTAS 2013); Jan. 1, 2013, 705-707. (Year: 2013).*
Li et al., Publication Date, A PDMS/Paper Hybrid Microfluidic Device Integrated With Graphene Oxide-Based Nano-Biosensors for Multiplexed Pathogen Detection, 17th International Conference on Miniaturized Systems for Chemistry and Life Sciences (MicroTAS 2013); Jan. 1, 2013, 705-707. (Year: 2013).*
Liu et al., A Portable Microfluidic Paper-Based Device for ELISA, 2011 IEEE 24th International Conference on Micro Electro Mechanical Systems (MEMS), Cancun, Mexico, 2011, 75-78 (Year: 2011).*
Kavruk et al., Portable Bioactive Paper-Based Sensor for Quantification of Pesticides, Journal of Analytical Methods in Chemistry, Jul. 1, 2013, 1-9. (Year: 2013).*
Lu et al., Patterned Paper as a Low-Cost, Flexible Substrate for Rapid Prototyping of PDMS Microdevices via "Liquid Molding", Analytical Chemistry, 2011, 83, 1830-1835. (Year: 2011).*
Lu et al., A Graphene Platform for Sensing Biomolecules, Angewandte Chemie Int. Ed., 2009, 48, 4785-4787. (Year: 2009).*
Zhang et al., Fabrication of Paper-Based Microfluidic Device Using Printed Circuit Technology, AIP Advances, 2012, 2, 1-7. (Year: 2012).*
Lin et al., A Simple Automated DNA Extraction Method for Dried Blood Specimens Collected on Filter Paper, Journal of Laboratory Automation, 2005, 10, 310-314. (Year: 2005).*
Corning, Corning and Falcon Microplates Selection Guide for Assay and Drug Discovery, Corning Life Sciences, 2011, A-30. (Year: 2011).*
Quraishi et al., The Use of Dried Blood Spot Samples in Screening Drugs of Abuse, Pharmacology & Pharmacy, 2013, 4,152-159. (Year: 2013).*

(Continued)

*Primary Examiner* — Amy M Bunker
(74) *Attorney, Agent, or Firm* — Norton Rose Fulbright US LLP

(57) ABSTRACT

Certain embodiments are directed to paper and its hybrid microfluidic devices integrated with nucleic acid amplification for simple, cost-effective, rapid, and sensitive pathogen detection, especially in low-resource settings.

10 Claims, 11 Drawing Sheets

Specification includes a Sequence Listing.

(56) References Cited

OTHER PUBLICATIONS

Skjaervo et al., Smart Blood Spots for Whole Blood Protein Analysis, Analyst, 2018, 143, 3184-3190. (Year: 2018).*
Whatman, Whatman Price Catalog, GE Life Sciences, 2014, 1-25. (Year: 2014).*
Brouwer et al. (2010) *Clin Microbiol Rev*, 23(3): 467-92.
Edgar et al. (2006) *Proc Natl Acad Sci USA*, 103(13).
Kovarik et al. (2011) *Analytical Chemistry*, 84: 516-40.
Martinez et al. (2008) *Lab Chip*, 8(12): 2146-50.
Nagdev et al. (2011) *J Clin Microbiol*, 49(5):1861-65.
Notomi et al. (2000) *Nucleic Acids Res*, 28(12): E63.
Panda et al. (2005) *J Clin Microbiol*, 43(6): 2895-2903.
Poppert et al. (2005) *J Clin Microbiol*, 43(7):3390-97.
Richardson et al. (2003) *J Clin Microbiol*, 41(8):3851-53.
Saleh et al. (2008) *Dis Aquat Organ*, 81(2): 143-51.
Smith and Burgoyne, (2004) *BMC Ecology*, 4(1): 4.
Ahmad et al. (2011) *Biomed Microdevices*, 13(5): 929-37.
Burr et al. (2001), *Plant Biol Rep*, 19: 367-71.
Chaisomchit et al. (2005) *Southeast Asian J Trop Med Public Health*, 36(1): 270-273.
Fang et al. (2012) *Lab on a Chip*, 12: 1495-99.
Ji et al. (2010) *Poult Sci*, 89(3): 477-83.
Ke et al. (2007) *Sensors and Actuators B: Chemical*, 120: 538-44.
Li and Li, (2010) *Expert Review of Clinical Pharmacology*, 3: 267-80.
Liu et al. (2011) *Lab Chip*, 11(6): 1041-48.
Loh et al. (2010) *Nat Chem*, 2(12): 1015-24.
Martinez, (2011) *Bioanalysis*, 3:2589-92.
Mori et al. (2001) *Biochem Biophys Res Commun*, 289(1): 150-54.
Salieb-Beugelaar et al. (2010), *Analytical Chemistry*, 82: 4848-64.
Smith et al. (2006) *Expert Rev Mol Diagn*, 6(2): 231-44.
Taton et al. (2000) *Science*, 289(5485): 1757-60.
Tsai et al. (2003) *Electrophoresis*, 24(17): 3083-88.
Vickers et al. (2011) *Eur J Clin Microbiol Infect Dis*, 30: 447-53.
Xia and Whitesides, (1998) *Rev. Mater. Sci.*, 1998: 31.

\* cited by examiner

METHODS AND COMPOSITIONS FOR PAPER-BASED AND HYBRID MICROFLUIDIC DEVICES INTEGRATED WITH NUCLEIC ACID AMPLIFICATION FOR DISEASE DIAGNOSIS

This application claims priority to U.S. Provisional Patent Application Ser. No. 62/022,879 filed Jul. 10, 2014, which is incorporated herein by reference in its entirety.

STATEMENT REGARDING FEDERALLY FUNDED RESEARCH

This invention was made with government support under Grant No. GM105584 awarded by the National Institute of Health. The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

The emergence of 335 infectious diseases in the human population has been reported between 1940 and 2004, which has caused an extremely significant impact on global health and economies (Jones et al. (2008) *Nature,* 45: 990-93; Morens et al. (2004) *Nature,* 430: 242-49). Among various global infectious diseases, epidemic meningitis is one of the most dangerous diseases. Epidemic meningitis is a severe and fast acting bacterial and/or viral infection of the brain and can become fatal as early as 24 hours after symptoms present. According to the World Health Organization, "Worldwide, without epidemics one million cases of bacterial meningitis are estimated to occur and 200,000 of these die annually . . . . Higher case-fatality rates (37-60%) have been reported in developing countries." (Castillo, *WHO Manual, 2nd Edition,* 2011). In addition, many case of meningitis occur in high-poverty areas, such as the "meningitis belt" of Africa where it remains an important and unresolved public health problem.

*Neisseria meningitidis,* the etiologic agent of meningococcal disease, is a leading cause of morbidity and mortality in children and young adults worldwide (Goldacre et al. (2003) *BMJ,* 327: 596-97; Heyderman et al. (2004) *Archives of Disease in Childhood,* 89: 1064-68). *N. meningitidis* is also the dominant etiologic agent in the meningitis belt according to bacteriologic and epidemiologic data over the past 30 years (LaForce et al. (2009) *Vaccine,* 27: Supplement 2, B13-B19). Along with *Neisseria meningitidis* (*N. meningitidis*), *Streptococcus pneumoniae* (*S. pneumoniae*), and *Haemophilus influenzae* type B (Hib) are the most common pathogens that cause bacterial meningitis. As a medical emergency, immediate antibiotic therapy is imperative, which must not be postponed by diagnostic delays. In addition, identification of the exact bacteria causing the disease is vital because treatment and antibiotics differ for each type. Due to the high fatality rate and the damaging effect that can be caused by untreated meningitis, considering many cases of meningitis cases occur in high-poverty areas, a simple, low-cost, highly-sensitive and specific approach for immediate multiplexed bacterial meningitis diagnosis is in great need for subsequent treatment.

SUMMARY

Microfluidics is a relatively new technique in the diagnostic research field that offers a unique opportunity for various biomedical applications (Li and Li, (2010) *Expert Review of Clinical Pharmacology,* 3: 267-80; Salieb-Beugelaar et al. (2010), *Analytical Chemistry,* 82: 4848-64; Kovarik et al. (2011) *Analytical Chemistry,* 84: 516-40). Microfluidics provides for minimal reagent consumption, integrated processing, and analysis of complex biological fluids with high efficiency and sensitivity. The devices and methods described herein provide for simple, rapid, and sensitive pathogen detection at low cost.

Certain embodiments are directed to microfluidic biochips that are either a paper-polymer hybrid system or a fully paper-based system. In certain aspects the biochips are low-cost, sensitive, and fast diagnostic devices for detecting infectious diseases. In certain aspects devices and methods described herein are used for detection of bacterial, fungal, viral, or parasite pathogens in remote and crude environments. In a further aspect, the devices and methods can be used, for example, to detect bacteria, such as those bacteria that cause meningitis, pertussis, and other infections. The devices and methods can be used to detect a number of pathogens.

Any suitable material or materials may be used to form the microfluidic device or components thereof (e.g., the top, middle, and/or bottom layers). In certain aspects the device may comprise one layer, two layers, three layers, or more. Each layer of a device can be comprised of multiple sublayers (e.g., a layer can be made of multiple sublayers of paper).

In certain embodiments the microfluidic device is partially paper or is an all paper device. Paper is a thin material produced by pressing together moist fibers, typically cellulose pulp derived from wood or grasses and drying them into flexible sheets. The thickness of paper is often measured by caliper, which is typically given in thousandths of an inch. Paper can be characterized by weight. In the United States, the weight assigned to a paper is the weight of a ream (500 sheets) before the paper is cut to size. For example, a ream of 20 lb, 8.5 in×11 in (216 mm×279 mm) paper weighs 5 pounds, because it has been cut from a larger sheet into four pieces. The density of paper ranges from 250 kg/m$^3$ (16 lb/cu ft) for tissue paper to 1,500 kg/m$^3$ (94 lb/cu ft) for some specialty paper. In certain aspect the paper is a porous blotting paper having a thickness of 0.5 to 2 mm, including all values there between. In a further aspect the paper is chromatography paper having a thickness 0.05 to 0.25 mm and pores having a diameter of 5 to 15 μm. The paper can be manufactured to be hydrophilic and interact with liquids and solutions in certain locations and treated in other areas so as to be hydrophobic. A paper microdevice can be designed to have hydrophobic regions that form channels and chambers that allow the flow of solutions within the microdevice. For example, the paper can be treated to be hydrophobic, e.g., treated with wax or other chemical that is integrated in the paper or coats the paper rendering it hydrophobic. Paper can be cut into appropriate shapes and/or layered so as to produce an all paper microfluidic device. In certain aspects the layer of a device can be comprised of a plurality of paper sublayers.

In certain aspects the device or components thereof may be fabricated from inorganic materials including glass, silica, silicon, metal, plastics or polymers, including dendritic polymers, such as poly(vinyl chloride), poly(vinyl alcohol), poly(methyl methacrylate), poly(vinyl acetate-maleic anhydride), poly(dimethylsiloxane)monomethacrylate, cyclic olefin polymers and copolymers including copolymers of norbornene and ethylene, fluorocarbon polymers, polystyrenes, polypropylene, polyethyleneimine; copolymers such as poly(vinyl acetate-co-maleic anhydride), poly (styrene-co-maleic anhydride), polysaccharide, polysaccharide peptide, poly(ethylene-co-acrylic acid) or derivatives of these or the like. The materials for forming the devices or components or parts thereof may be selected based on desired mechanical or other properties for optimizing target detection. In certain aspects the device is made, in part, of a polymer, such as but not limited to polysiloxane (e.g., polydimethysiloxane (PDMS)); polymethyl-methacrylate (PMMA), polycarbonate (PC), or cyclic olefin copolymer (COC). In further aspects a layer of the device (e.g., a middle layer) can be a siloxane polymer, such as, but not limited to polydimethysiloxane (PDMS). In certain aspects a support layer or bottom layer can be glass, PMMA, PDMS, PC, or COC.

In certain aspects the microfluidic biochip can comprise one or more microwells or chambers position in 1, 2, 3, or more layers of the device (device layers). A microwell can be 0.5, 1, 2, or 3 mm in diameter, including all values there between and 1, 2, 3, or 4 mm in depth, including all values there between. In certain aspects a microwell can be cut into a paper layer or sublayers of a paper layer. In certain aspects various microwells can be fluidically connected by microchannels. In certain aspects the device can be loaded without using complicated surface modification procedures for probe immobilization by using a paper floor of the well or a paper insert with reagents. In further aspects the detection wells can be linked or fluidically connected to reagent delivery channel(s). In certain aspects a reagent mixture (e.g., a probe and/or amplification mixture) can be preloaded into microwells. In certain aspect a probe is coupled to a detectable label, e.g., a fluorescent label. In a further aspect probe can be reversibly complexed or absorbed in a quenching moiety that dissociates from the probe forming a fluorescent moiety. In certain aspects the quenching moiety is manganese or graphene oxide. Certain embodiments are directed to a device having at least one microwell that is configured so that the signal generated that is detectable by the human eye, i.e., a signal is detectable upon visual inspection. In certain aspects amplification and detection are performed in a single well. In further aspects a mobile computing device can be used as a detector. In certain aspects a smartphone or tablet camera can be used as a detector.

In one aspect, at least one microwell is configured as an amplification well. In certain aspects the amplification well will comprise one or more primer pairs, with each primer pair being specific for a microbe or a family or genus of microbes. A test sample can be loaded into the amplification well. In certain embodiment pathogens are directly detected without any complicated DNA treatment such as DNA extraction and/or purification. The amplification well can also include enzymes, substrates, and other components for amplification. Therefore, embodiments of the device provide a one-step mechanism with high sensitivity for pathogen detection.

One embodiment is a single chamber amplification/detection microfluidic device wherein amplification and detection are carried out in a single chamber. In certain aspects a microfluidic system has an amplification/detection chamber configured to amplify nucleic acids and detect amplified nucleic acids in a single chamber. In certain aspects, nucleic acid amplification methods can be loop-mediated isothermal amplification (LAMP) or other isothermal gene amplification methods. The detection moiety can be a probe that binds an amplification product or other chemical that reacts or is detectably transformed when amplification occurs in the amplification well. In certain aspects a microfluidic system has multiple single chamber amplification/detection chambers configured to amplify nucleic acids and detect amplification of nucleic acids for detecting multiple pathogens, each pathogen detected by a separate chambers or a plurality of pathogens can be detected in one or more chambers. This embodiment can be referred to as a dual-purpose chamber microdevice. In certain aspects the single chamber device comprises a non-specific labeling agent (e.g., calcein or a similar compound that is liberated when amplification occurs, or that associates with an amplicon generating a detectable signal) that will detect the production of an amplicon or the occurrence of amplification in the amplification chamber. In other aspects a specific hybridization probe can be included in the chamber that binds to a specific amplified nucleic acid.

In certain aspects an amplification system can include a heating layer, such as a battery-powered heating layer that can produce temperature sufficient for amplification. The heater will comprise a battery interface coupled to a heating element. In certain aspects the heating layer is integrated with the microfluidic device and is configured to heat the amplification well. In another aspect the heater is a separate component that can be re-used with multiple microfluidic devices.

Another embodiment is directed to a microdevice that has one chamber for amplification and at least a second chamber for detection. The amplification chamber and the detection chamber can be positioned in the same or different layers of the device. Certain aspects include a microfluidic system comprising an amplification chamber in one layer and a separate detection chamber in a second layer. The amplification chamber can be configured so that after the amplification process the amplified sample is transferred to one or more detection zones. Alternatively the amplification chamber can be configured as a detection zone as well. The detection zones will have one or more specific probes that will specifically bind a target amplicon derived from a specific microbe or class of microbes. In certain aspect, the detection wells can be configured on the same (e.g., a single layer configuration) or different layer (e.g., a multi-layer configuration) with respect to the amplification wells. In certain aspects, a piece of paper can be inserted to each detection well. The paper insert can be used to immobilize DNA capture probes, provide amplification primers, and other amplification or detection reagents. Certain embodiments are directed to a detector configured to detect the presence of a target by detecting the interaction between a probe and a target using a device described herein.

Certain embodiments are directed to methods of detecting a target or pathogen comprising introducing a sample suspected of having or comprising a target or pathogen into a device described herein and subjecting the sample to nucleic acid amplification, wherein if a target is present in the sample its nucleic acid is amplified and the amplified nucleic acid binds to a probe and produces a detectable signal. In certain embodiments the device is configured to function as a stand-alone device not needing other machines or device for operation. In certain aspect the device can comprise a battery. In certain aspects the device is configured to detect a plurality of targets at once (multiplexed assay) with a separate and distinct probe in an individual detection microwell. In certain aspects a single detection microwell can have two or more probes that can be distinguish from each other. In certain aspects the target is a pathogen, such as a food borne pathogen. The pathogen can be a bacteria, a fungus, a parasite, a virus, or combinations thereof. The sample can comprise a lysis agent to expose nucleic acid to an amplification mixture. A pathogen can be lysed using a centrifugation free lysis method, heating the pathogen, or using a centrifugation free lysis method and heating the pathogen.

The term "probe" refers to a molecule that can detectably distinguish between target molecules differing in structure/ nucleic acid sequence. Detection can be accomplished based on identification of specific binding with a target. Examples of such specific binding include nucleic acid probe hybridization. Thus, for example, probes can include nucleic acid hybridization probes, for example DNA, RNA, PNA, pseudo-complementary PNA (pcPNA), locked nucleic acid (LNA) and nucleic acid analogs thereof.

Oligonucleotides can be used as "probes", and refer to e.g., synthetic nucleic acids, genomic DNA, mRNA, or other suitable sources of nucleic acid oligonucleotides. For such purposes, the oligonucleotides must be capable of specifically hybridizing to a target polynucleotide or DNA molecule. As used herein, two nucleic acid molecules are said to be capable of specifically hybridizing to one another if the two molecules are capable of forming an anti-parallel, double-stranded nucleic acid structure under hybridizing conditions.

The phrase "specifically binds" to a target refers to a binding reaction that is determinative of the presence of the target in the presence of a heterogeneous population of other biologics. Thus, under designated hybridization conditions, a specified molecule binds preferentially to a particular target and does not bind in a significant amount to other biologics present in the sample.

As used herein, the term "sample" or "test sample" generally refers to a material suspected of containing one or more targets. The test sample may be used directly as obtained from the source or following a pretreatment to modify the character of the sample. The test sample may be derived from any biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid or the like. The test sample may be pretreated prior to use, such as preparing plasma from blood, diluting viscous fluids, lysing or disrupting microbes in the sample, and the like. Methods of treatment may involve shearing, filtration, precipitation, dilution, distillation, mixing, concentration, inactivation of interfering components, lysing organisms and/or cells, and the addition of reagents. Besides physiological fluids, other samples may be used such as water, food products, and the like for the performance of environmental or food production assays. In addition, a solid material suspected of containing the target may be used as the test sample. In some instances it may be beneficial to modify a solid test sample to form a liquid medium or to release a target (e.g., a nucleic acid).

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figures 1A, 1B, 1C:
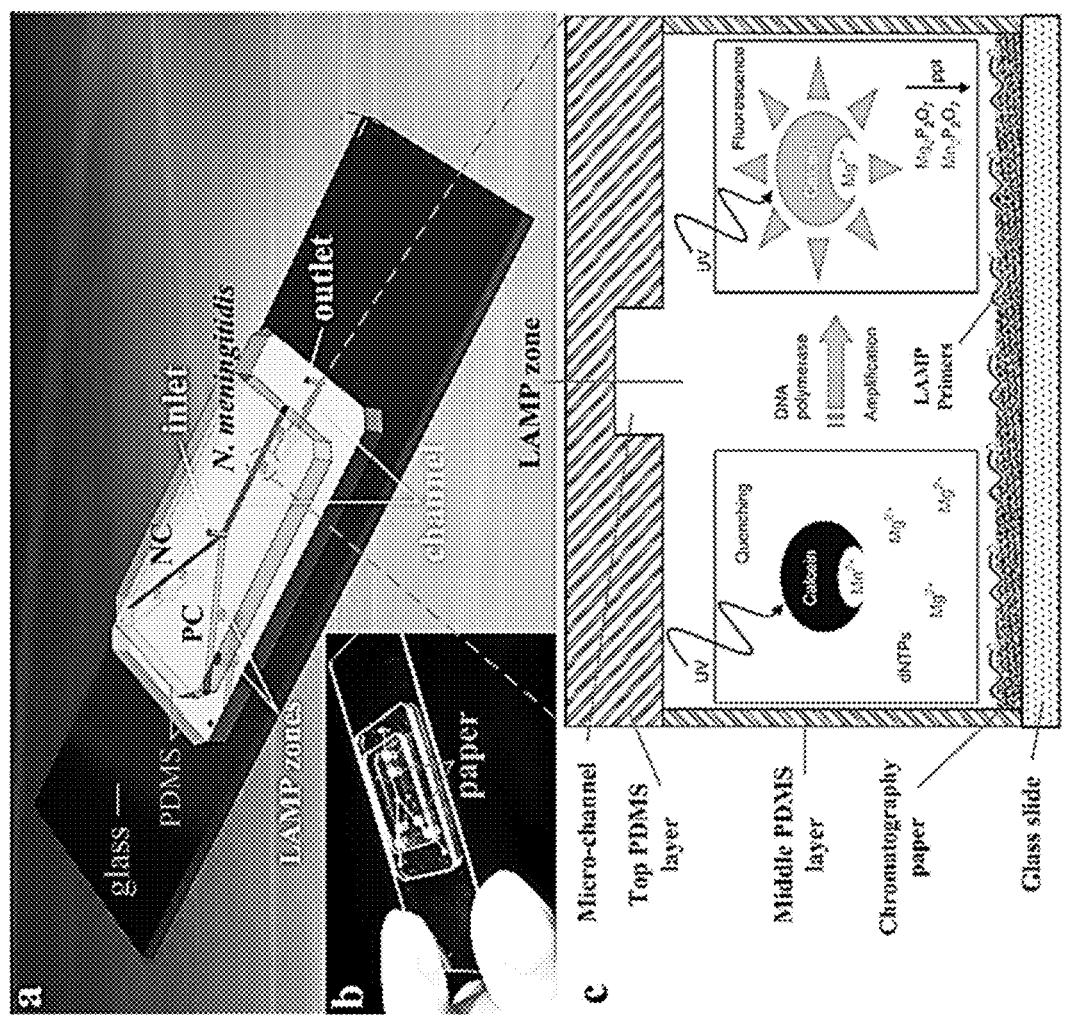
FIG. 1A-1C. Chip layout of the PDMS/paper hybrid microfluidic device for singleplexed pathogen detection. (a) 3D illustration of the schematic of the chip layout. The chip consists of one top PDMS layer, one middle PDMS layer and one glass slides for reagent delivery, LAMP reaction and structure support, respectively. A chromatography paper disk is situated inside each LAMP zone to preload LAMP primers. (b) A photograph of the hybrid microfluidic device for infectious disease diagnosis. (c) A cross-section view of the LAMP zone illustrating the principle of the LAMP detection.

There are several laboratory guidelines available from the Centers for Disease Control and Prevention (CDC) and the WHO for the diagnosis of meningitis. Gram stain and cell culture are the most commonly used approaches for meningitis diagnosis (Brouwer et al. (2010) *Clin Microbiol Rev,* 23(3): 467-92). However, both have to be done in laboratories, and the processes are costly and time consuming, especially for cell culture. Although gram stain seems to be a relatively faster process after reaching the laboratory, it still has many limitations: (1) Gram stain is not reliable, since the absence of bacteria does not exclude bacterial meningitis as bacteria are seen in only 60% of cases; this figure is reduced by a further 20% if antibiotics were administered before the sample was taken. (2) Gram stain's detection sensitivity is low. (3) The gram stain approach needs well-trained personnel, due to the fact that sometimes poor staining occurs. Only a few poorly staining bacteria may be present on an entire slide, and inflammatory cells, erythrocytes, stained protein, and precipitated stain may obscure the bacteria. According to one study in 2008 by Nueman, up to 40% of cases of positive gram stain results can be due to contamination or misinterpretation (Neuman et al. (2008) *Pediatr Infect Dis J,* 27(4):309-13). Spinal tap or lumbar puncture is another diagnostic procedure to collect cerebrospinal fluid (CSF) for the meningitis examination, but it is an invasive procedure and can be only done by trained personnel.

Recently, real-time polymerase chain reaction (qPCR) (Poppert et al. (2005) *J Clin Microbiol,* 43(7):3390-97; Richardson et al. (2003) *J Clin Microbiol,* 41(8):3851-53), conventional loop mediated isothermal amplification (LAMP) (Nagdev et al. (2011) *J Clin Microbiol,* 49(5):1861-65), and latex agglutination tests have been reported to provide faster detection of bacterial meningitis than cell culture. *Neisseria meningitidis, Haemophilus influenzae,* and *Streptococcus pneumonia* are the three main bacterial pathogens that cause meningitis (Castillo, Laboratory Methods for the Diagnosis of Meningitis caused by *Neisseria meningitidis, Streptococcus pneumoniae,* and *Haemophilus*

*influenzae*. In: WHO Manual, 2nd Edition. Harcourt, B (Ed. (World Health Organization, Center for Disease Control and Prevention, 2011)). The treatment for different types of bacteria varies. Therefore, it is important to know what type of bacterial meningitis before immediate and effective treatment. Nevertheless, most approaches do not provide multiplex diagnosis function. Nagdev et al. (2011) have reported an off-chip LAMP amplification method for the clinical diagnosis of meningitis, but only one type of bacterial meningitis (Tuberculosis Meningitis) can be detected and it needs a Loopamp real-time turbidimeter (Nagdev et al. (2011) *J Clin Microbiol*, 49(5):1861-65). Furthermore, these tests require expensive specialized equipment in laboratories, such as thermal cyclers, turbidimeters, centrifuges, fluorescence microscopes, and so on, which limits the applications of those approaches in low-resource settings.

Certain embodiments are directed to a low-cost point of care (POC) device for rapid and high-sensitivity pathogen detection in resource-poor settings. Certain aspects provide a low cost approach for microbe detection through the use of paper-based microfluidics, e.g., all-paper microfluidic devices. Because of the miniaturization of reactions carried out in microfluidic systems, low reagent consumption is an intrinsic advantage that reduces costs associated with reagents and materials. In addition, paper is inexpensive and easy to obtain. The material cost for an all paper-based microfluidic device is only a few cents (Martinez et al. (2008) *Lab Chip*, 8(12): 2146-50).

Certain devices and methods described herein are faster, compared to conventional detection methods, such as cell culture. In certain aspects a device described herein can be configured to detect meningitis-causing organisms. Rapid assay is crucial in meningitis diagnosis. The assay based on LAMP takes only ~45 min to finish (Saleh et al. (2008) *Dis Aquat Organ*, 81(2): 143-51), which ensures the best chance for faster patient care and complete recovery. Certain embodiments can provide higher detection sensitivity than conventional meningitis diagnosis methods, due to the integration of DNA amplification on a chip, which can provide sensitivity close to the single-pathogen detection level—providing for early diagnosis of meningitis.

The integrated, multiplexed function of certain paper-based devices described herein allow for simultaneous testing of at least one, two, three or more pathogens, eliminating the need for separate laboratory testing for each pathogen. Certain aspects require minimal instrument demands and no specialized equipment, such as a thermal cycler and centrifuge. Certain aspects utilize a fluorescent or a colorimetric assay that is detectable by the naked eye, bringing the advantages of sensitive and efficient microfluidics analysis directly to the patient's POC. In certain aspects there is no need for a detector, other than the human eye. In a further aspect the a light pen, laser pointer, or equivalent device can be used to illuminate a detectable sample.

Paper-based microfluidic devices can have certain beneficial features, including, but not limited to: (i) They are disposable, avoiding the spread of infectious diseases from used devices; (ii) fabricating paper-based devices is simple and does not require the use of clean-room facilities; (iii) Paper has good stackability, allowing the formation of 3D structures readily for complex assays; (iv) The high surface-to-volume ratio provided by the macroporous structure in the paper material improves DNA hybridization kinetics, allowing fast pathogen detection; and (v) Paper provided much more stable testing results than without paper over a period of two months (FIG. 6).

I. MICROFLUDIC DEVICE

As shown in FIG. 1, certain embodiments of a microfluidic device for singleplexed pathogen detection can comprise at least three layers. Other embodiments can be single layer or two layer devices. The top layer can be a polymer layer used for reagent delivery, three micro-channels are formed in the top layer illustrated in FIG. 1. Also formed in the top layer is an inlet reservoir. The middle layer is a polymer layer having two or more loop-mediated isothermal amplification (LAMP) zones, outlet reservoirs and microchannels downside, which are used for LAMP reaction and detection. The bottom layer is a support layer (e.g., a glass slide (length 75 mm, width 25 mm, depth 1.0 mm). Different LAMP zones can be used for negative control (NC), positive control (PC) and pathogen detection.

The detection portion of the device comprises specific primers and/or specific probes for target pathogens or positive control DNA can be pre-loaded in the amplification chamber. In certain aspects an amplification chamber can be loaded with 1, 2, 3, 4, or more primer pairs. In certain aspects amplification and detection are performed in a single chamber. In a further aspect, an amplification reaction is transferred to a separate detection zone, e.g., by puncturing a wall of the amplification chamber and allowing the flow of amplicons to a detection region of the device. A device can be configured to transport a reaction mixture and/or sample from an inlet to fill the amplification chamber/zones. In certain aspect a filter is included in the device and positioned such that a sample being applied to the device is filtered prior to being transported to an amplification chamber/zone. After filling, the inlet and outlets can be sealed, e.g., with epoxy. Amplification is then performed at an appropriate temperature on a heating film for an appropriate amount of time.

As shown in FIG. 2, certain embodiments of a microfluidic device with more channels and LAMP zones for multiplexed pathogen detection can comprise at least three layers. Microfluidic devices and systems can be configured to perform numbers of different analytical and/or synthetic operations within the confines of very small channels and chambers that are disposed within small scale integrated microfluidic devices. Multiplexing the basic system can substantially increase throughput, so that the operations of the system are carried out in highly parallelized system.

Microfluidic devices and systems, because of their extremely small space requirements are particularly well suited for parallelization or multiplexing because large numbers of parallel analytical fluidic elements can be combined within a single integrated device that occupies a relatively small area. A parallelized or multiplexed device can be configured for high throughput screening assays. A multiplexing system will comprise a plurality of channels and microwells that are configured to analyze a number of different pathogens.

Figures 10A, 10B, 10C:
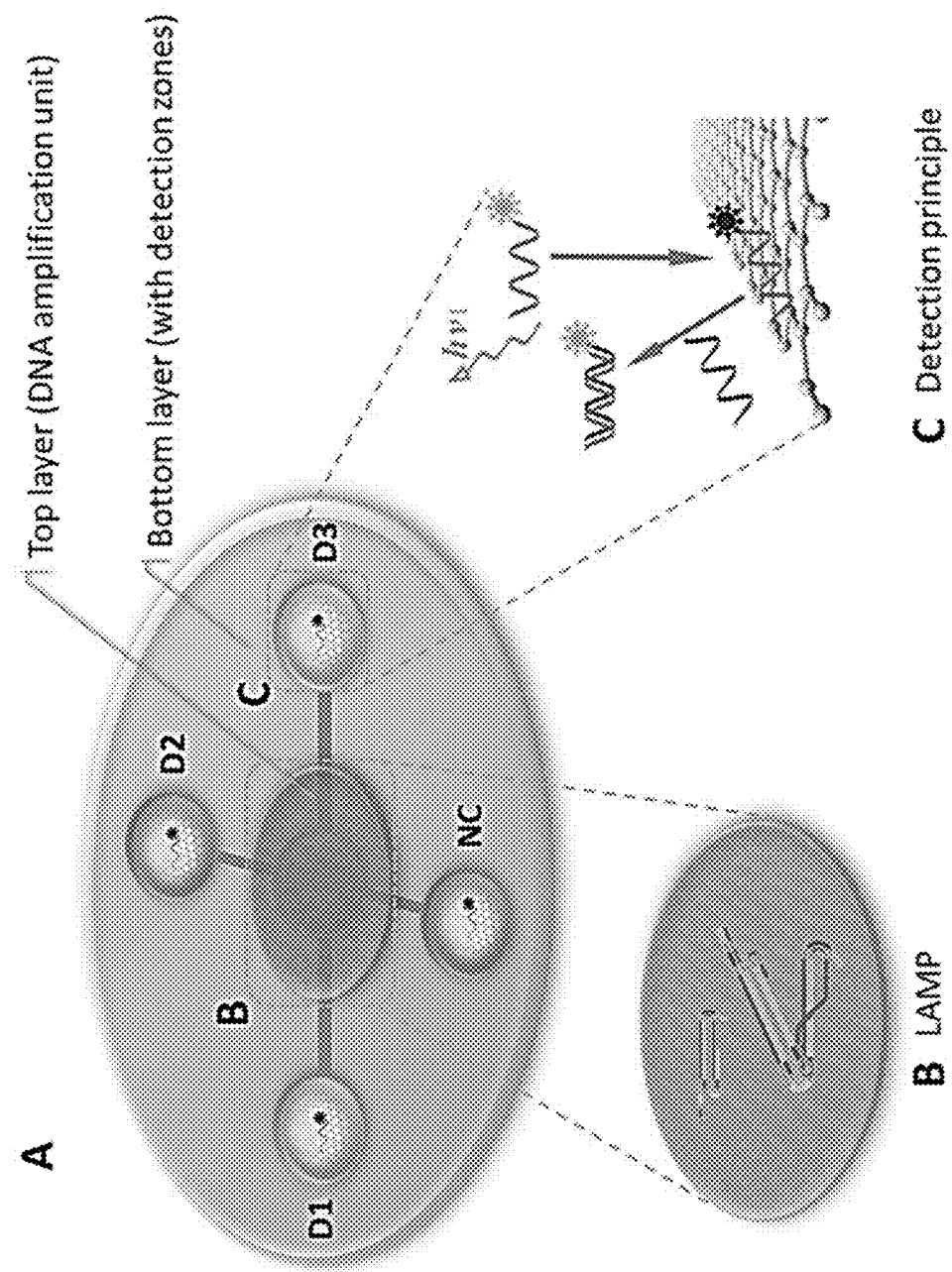
FIG. 10A-10C. (A-C) Schematic of low-cost and multiplexed detection of meningitis causing pathogens on paper-based 3D microfluidic devices. There are two layers in the microfluidic system. DNA amplification unit—LAMP is carried out in the top layer. (C) Illustration of detection principle using graphene-oxide nano-material. Fluorescence of fluorophore-labeled probes is quenched when probes are adsorbed on the surface of grapheme oxide (GO). In contrast, when the target DNA is present, the quenched fluorescence is restored.

In certain embodiments a paper-based microfluidic device may comprise at least two layers (FIG. 10), one layer having an amplification chamber and a second layer having a detection zone. The top layer can be nucleic acid amplification unit. The bottom paper layer can include microchannels and detection zones. In certain aspects the bottom layer comprises 2, 3, 4, 5, 6, or more microchannels. The microchannels can be in fluid communication with 2, 3, 4, 5, 6 or more detection zones. Each detection zone can have one or more detectable probes. In certain aspects the detectable moiety of the detectable probe is quenched. In certain aspects the detectable moiety is quenched by graphene oxide.

Figures 11A, 11B:
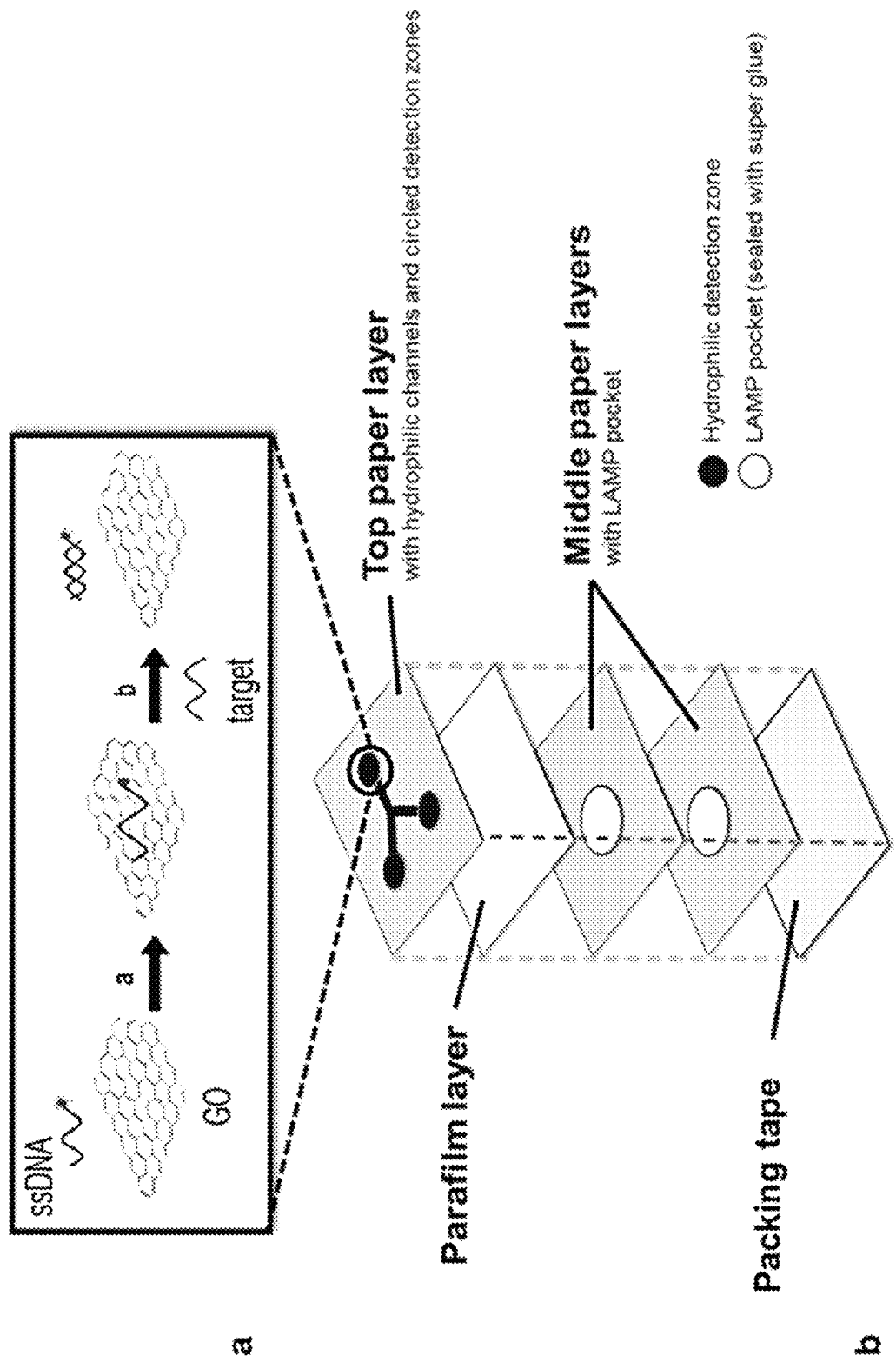
FIG. 11A-11B. 3D schematic illustration of a paper-based LAMP biochip integrated with DNA capture probe-based detection wells for high-sensitivity quantitative disease diagnosis. Detection principle is illustrated in the inset.

In certain embodiments a paper-based microfluidic device may comprise multiple layers to form at least one DNA amplification well (FIG. 11), and one layer having an at least one detection zone. In certain aspects the detection layer comprises 2, 3, 4, 5, 6, or more microchannels. The microchannels can be in fluid communication with 2, 3, 4, 5, 6 or more detection zones. An insulation layer can be added between the detection layer and amplification zones to prevent reagent loss. Each detection zone can have one or more detectable probes. In certain aspects the detectable moiety of the detectable probe is quenched. In certain aspects the detectable moiety is quenched by graphene oxide.

Integration of DNA Amplification on Chip.

To increase the detection sensitivity and avoid contamination during sample transfer, certain embodiments have a DNA amplification unit or amplification chamber/zone integrated on the device. This chamber, unit, or zone can be provided on a separate layer of paper providing flexibility in sample handling. In certain aspects the bottom of the DNA amplification zone is sealed, for example with a thin layer of adhesive tape, and the top is covered with a tape layer, a cap or mineral oil to prevent liquid evaporation. Next, DNA samples are isothermally amplified at about 63° C. on a thin film heater by LAMP (Ahmad et al. (2011) *Biomed Microdevices*, 13(5): 929-37). In certain aspects, a portable heating system based on a proportional-integral-derivative (PID) temperature controller (Auber Inst, GA.), a thermocouple (Auber Inst.), and a heating film (Omega, CT) can be used. A battery-powered portable heating system can be used for field detection. During the DNA amplification process, the pathogen DNA can be labeled with fluorophores for DNA fluorescence detection in a later step.

Conventional DNA PCR amplification requires a carefully controlled sequence of heating and cooling cycles. The fabrication of heaters and temperature sensors on chip is complicated (Liu et al. (2011) *Lab Chip*, 11(6): 1041-48). In contrast, certain embodiments of the LAMP method utilizes the *Bacillus stearothermophilus* DNA Polymerase, a thermally-stable enzyme with high displacement ability over the template-primer complex (Saleh et al. (2008) *Dis Aquat Organ*, 81(2): 143-51; Notomi et al. (2000) *Nucleic Acids Res*, 28(12): E63). This DNA amplification technique allows nucleic acid amplification to be carried out under thermally constant conditions, eliminating the use of expensive and cumbersome thermal cycler equipment in low-resource settings. The heating system is small enough to be placed in one's pocket and can be used in conjunction with a portable battery-powered heating system.

Certain aspects described herein link graphene oxide (GO) to the paper substrate by a physical absorption method or covalent surface modification of paper. For surface modification, 3-aminopropyl-trimethoxysilane (APTMS) is immobilized on the paper surface by linkage with hydroxyl groups. The reaction of carboxyl groups from GO with amine groups from APTMS leads to the covalent attachment of GO on the paper surface. Once GO is linked to the paper in the detection zones, it will provide a platform on which to immobilize various DNA probe oligonucleotides (e.g., 5'-AACCTTGAGCAATCCATTTATCCTGACGTTCT-3' (SEQ ID NO:1), 5'-GCGGATTCCCAGTT-GAGTGTGCGTGTAC-3'(SEQ ID NO:2), 5'-TGGTGCTAAGATGAAGTTATGGC-3'(SEQ ID NO:3), for *N. meningitidis*, *H. influenzae* and *S. pneumonia*, respectively, for multiplex DNA sensing. ssDNA labeled with fluorophores can self-assemble onto the surface of GO to form a stable ssDNA-GO architecture, and its fluorescence will be quenched (Loh et al. (2010) *Nat Chem*, 2(12): 1015-24).

In certain aspects, after DNA amplification, the seal underneath the DNA amplification zone will be penetrated and fluid communication with a channel on the bottom layer of paper established. In certain aspects DNA amplicons flow to different detection zones via the wicking effect of paper. This provides a simple strategy to actuate liquid flows in paper, without off-chip controllers and power. This feature can be useful for detection in the field and other resource-limited settings. Specific DNA capture probes targeted to different pathogens will be pre-adsorbed in the detection zones (e.g., via GO), allowing the detection of pathogens via DNA hybridization, simultaneously, and selectively.

Certain embodiments incorporate a miniaturized portable fluorescence detection system using a light emitting diode (LED), such as violet LED (Tsai et al. (2003) *Electrophoresis*, 24(17): 3083-88), a UV LED, or a green laser pointer. The wavelength of 532 nm from a green laser pointer is a good fit with the excitation wavelength of one of the common probes—Cy3, but other combinations of light source and fluorophore can be used. A brief comparison among different diagnostic approaches is listed in Table 1.

TABLE 1

Comparisons among different diagnostic approaches

| | Chip material cost | Heating system | Detection | For resource-poor settings | Time needed |
|---|---|---|---|---|---|
| Ours | ~5 cents | ~$70 | ~$ 150 | Yes | <60 min |
| qPCR | N/A | ~$65,000 | | No | 2-30 hours |
| Cell culture | N/A | ~$7,000, incubators | ~$6,000 | No | >48 hours |

Instrument-Free Detection of Amplified Target DNA.

Certain embodiments incorporate a visual fluorescent or a colorimetric detection method. Mori et al (2001) observed that during the LAMP amplification process, a magnesium pyrophosphate precipitate was formed as a turbid by-product of the nucleic acid amplification process (Mori et al. (2001) *Biochem Biophys Res Commun*, 289(1): 150-54). This precipitate forms only when the targeted DNA is present in the LAMP amplification process, such that the presence of the pyrophosphate can serve as an indicator of the presence of a pathogen's target DNA. Visual confirmation by the naked eye can be achieved by the addition of an intercalating dye, SYBR green I, to detection zones (Ji et al. (2010) *Poult Sci*, 89(3): 477-83), that turns green in the presence of targeted pathogen DNA under normal light, while the original orange color is retained for a negative control (Parida et al. (2005) *J Clin Microbiol*, 43(6): 2895-2903). As such, clinical diagnosis of a pathogen (e.g., meningitis-causing pathogen) can be achieved by visual confirmation of the green color formed. This method will allow for a simplified instrument-free, multiplexed one-step visual determination of the presence of three meningitis-causing pathogens.

In certain embodiments a filter or filtration layer can be included to remove red blood cells in order to avoid detection inference in subsequent steps.

Certain configurations of the device include multiple nucleic acid amplification zones. These nucleic acid amplification zones can be dual function amplification/detection zones. Blood samples from individuals can be collected using a sample inlet that is loaded by pricking a finger with a lancet and applying blood drop similar to glucose testing using a POC glucometer. The filtration layer can remove blood cells. Bacterial cells can be lysed and DNA extracted using a new lysis buffer that we developed (lysis buffer (50 mM Tris buffer (pH 7.5), 4 M urea and 0.1% triton) which is fully compatible to LAMP reactions, while many others completely inhibited LAMP reaction, or by heating the sample to a high temperature (e.g. 95° C.) using a battery-powered portable heating system. In certain aspects different detection zones will have different primers. Different primers for different pathogen targets will be pre-loaded in the different detection zones. When the appropriate DNA is present, the primers interact with the sample. LAMP will only occur when the pathogen and the pathogen-specific primers are present enabling the test to be highly specific, as shown by a precipitate in different detection zones, or green fluorescence if calcein is used.

In certain embodiments a microfluidic device is configured for meningitis diagnosis in a laboratory or home setting. In other embodiments a microfluidic device is configured to provide a POC device for field diagnosis. Furthermore, the microfluidic devices and methods presented will be used to detect various plant, animal, food-borne, and other infectious diseases (e.g., *B. pertussis*, HIV) in resource-limited settings.

Colorimetric detection can be enhanced by UV light from UV LED, gold nanoparticles, quantum dots (QDs) (Edgar et al. (2006) *Proc Natl Acad Sci USA*, 103(13): 4841-45; Smith et al. (2006) *Expert Rev Mol Diagn*, 6(2): 231-44), and silver enhancement (Taton et al. (2000) *Science*, 289(5485): 1757-60) can be used as detectable moieties. Gold nanoparticles promote the reduction of $Ag^+$, resulting in the color change from white to black on paper.

In certain aspects GO is immobilized on the paper surface to adsorb DNA capture probes. If the efficiency of GO immobilization on paper is sufficient, a covalent immobilization of DNA capture probes can be used to graft DNA codes on paper. In certain aspects DNA capture probes can be immobilized on paper directly without using GO.

Probes can be coupled to a variety of reporter moieties. Reporter moieties include fluorescent reporter moieties that can used to detect aptamer binding to a target. Fluorophores can be fluorescein isothiocyanate (FITC), allophycocyanin (APC), R-phycoerythrin (PE), peridinin chlorophyll protein (PerCP), Texas Red, Cy2, Cy3, Cy3.5, Cy5, Cy5.5, Cy7; or fluorescence resonance energy tandem fluorophores such as PerCPCy5.5, PE-Cy5, PE-Cy5.5, PE-Cy7, PE-Texas Red, and APC-Cy7. Other fluorophores include, Alexa Fluor® 350, Alexa Fluor® 488, Alexa 25 Fluor® 532, Alexa Fluor® 546, Alexa Fluor® 568, Alexa Fluor® 594, Alexa Fluor® 647; BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665; Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, and tetramethylrhodamine, all of which are also useful for fluorescently labeling nucleic acids.

In certain aspects the fluorescence of a probe can be quenched. Quenching refers to any process that decreases the fluorescence intensity of a given substance. A variety of processes can result in quenching, such as excited state reactions, energy transfer, complex-formation, and collisional quenching. Molecular oxygen, iodide ions, and acrylamide are common chemical quenchers. The chloride ion is a well-known quencher for quinine fluorescence. Typically quenching poses a problem for non-instant spectroscopic methods, such as laser-induced fluorescence, but can also be used in producing biosensors. In certain aspects the fluorescence of a labeled probe that is not bound to its target is quenched, wherein upon binding to its target the fluorescence is recovered and can be detected. The labeled probe is complexed with a quenching moiety while absorbed onto the paper layer of a device as described herein. Once the probe binds its target the fluorescence is recovered. Target binding results in recovered fluorescence.

In certain aspects the fluorescence can be quenched by forming a probe/graphene oxide complex. In certain aspects the probe/graphene oxide complex is adsorbed to a paper substrate or layer. Graphene oxide (GO) is a compound of carbon, oxygen, and hydrogen in variable ratios, obtained by treating graphite with strong oxidizers. Graphene oxide (GO) is an intermediate on the route to chemically derived graphene, and it is easily synthesized. Its chemical structure is heterogeneous and consists of both large areas of conjugated sp2-systems and various electronically isolated oxygen containing functionalities. GO can act as a quencher of fluorescence and is easily dispersible in water. In certain aspects the quencher can be graphene, graphene oxide, carbon nanotubes, carbon nanoparticles or other materials. In some instances the binding of the target results in desorption of the probe, which in turn results in an increase in fluorescence.

II. PATHOGENIC MICROBES

In one embodiment, the invention concerns rapid and accurate methods for detecting food-borne pathogens, including without limitation, parasites and their eggs, Noroviruses (Norwalk-like viruses), *Campylobacter* species, *Giardia lamblia, Salmonella, Shigella, Cryptosporidium parvum, Clostridium* species, *Toxoplasma gondii, Staphylococcus aureus*, Shiga toxin-producing *Escherichia coli* (STEC), *Yersinia enterocolitica, Bacillus cereus, Bacillus anthracis, Cyclospora cayetanensis, Listeria monocytogenes, Vibrio parahemolyticus* and *V. vulnificus*. The term "microorganism" or "microbe" as used in this disclosure includes a virus, bacterium, fungi, parasite, or parasite's egg.

In certain aspects a pathogenic or potentially pathogenic microbe can be detected. A pathogenic microbe can be a virus, a bacterium, and/or a fungus. In certain aspects the device can be configured to detect a variety of microbes include viruses, bacteria, and fungi simultaneously. In certain aspects, a microbe includes a virus. The virus can be from the Adenoviridae, Coronaviridae, Filoviridae, Flaviviridae, Hepadnaviridae, Herpesviridae, Orthomyxoviridae, Paramyxovirinae, Pneumovirinae, Picornaviridae, Poxyiridae, Retroviridae, or Togaviridae family of viruses; and/or Parainfluenza, Influenza, H5N1, Marburg, Ebola, Severe acute respiratory syndrome coronavirus, Yellow fever virus, Human respiratory syncytial virus, Hantavirus, or Vaccinia virus.

In yet a further aspect, the pathogenic or potentially pathogenic microbe can be a bacteria. A bacterium can be an intracellular, a gram positive, or a gram negative bacteria. In a further aspect, bacteria include, but is not limited to a *Neisseria meningitidis* (*N. meningitidis*), *Streptococcus pneumoniae* (*S. pneumoniae*), and *Haemophilus influenzae* type B (Hib), *B. pertussis, B. parapertussis, B. holmesii*,

*Escherichia*, a *Staphylococcus*, a *Bacillus*, a *Francisella*, or a *Yersinia* bacteria. In still a further aspect, the bacteria is *Bacillus anthracis, Yersinia pestis, Francisella tularensis, Pseudomonas* aerugenosa, or *Staphylococcus aureas*. In still a further aspect, a bacteria is a drug resistant bacteria, such as a multiple drug resistant *Staphylococcus aureas* (MRSA). Representative medically relevant Gram-negative bacilli include *Hemophilus influenzae, Klebsiella pneumoniae, Legionella pneumophila, Pseudomonas aeruginosa, Escherichia coli, Proteus mirabilis, Enterobacter cloacae, Serratia marcescens, Helicobacter pylori, Salmonella enteritidis*, and *Salmonella typhi*. Representative gram positive bacteria include, but are not limited to *Bacillus, Listeria, Staphylococcus, Streptococcus, Enterococcus, Actinobacteria* and *Clostridium Mycoplasma* that lack cell walls and cannot be Gram stained, including those bacteria that are derived from such forms.

In still another aspect, the pathogenic or potentially pathogenic microbe is a fungus, such as members of the family *Aspergillus, Candida, Crytpococus, Histoplasma, Coccidioides, Blastomyces, Pneumocystis*, or *Zygomyces*. In still further embodiments a fungus includes, but is not limited to *Aspergillus fumigatus, Candida albicans, Cryptococcus neoformans, Histoplasma capsulatum, Coccidioides immitis*, or *Pneumocystis carinii*. The family zygomycetes includes Basidiobolales (Basidiobolaceae), Dimargaritales (Dimargaritaceae), Endogonales (Endogonaceae), Entomophthorales (Ancylistaceae, Completoriaceae, Entomophthoraceae, Meristacraceae, Neozygitaceae), Kickxellales (Kickxellaceae), Mortierellales (Mortierellaceae), Mucorales, and Zoopagales.

III. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Singleplexed Detection

A. Methods and Materials
LAMP Detection:

The LAMP primers for the target ctrA gene sequence from *Neisseria meningitidis*, as shown in Table 2. Loopamp DNA amplification kit and Loopamp fluorescence detection reagent (calcein) were purchased from Eiken Co. Ltd., Japan. The Loopamp reaction mixture contained 20 mM Tris-HCl (pH 8.8), 10 mM KCl, 8 mM $MgSO_4$, 10 mM $(NH_4)_2SO_4$, 0.1% Tween 20, 0.8 M Betaine, 0.5 mM $MnCl2$, 1.4 mM dNTPs, 8U Bst Polymerase, 1.6 µM each of the inner primer (FIP/BIP), 0.2 µM each of the outer primer (F3/B3), 0.4 µM each of the loop primer (LF/LB).

Microfluidic Platform Fabrication:

Polydimethylsiloxane (PDMS, Sylgard 184) was obtained from Dow Corning (Midland, Mich.), Whatman chromatography paper was purchased from Sigma (St. Louis, Mo.), Epoxy was purchased from ITW Devcon (Danvers, Mass.).

DNA Isolation:

DNA isolation kit and LAMP product purification kit were purchased from Qiagen (Valencia, Calif.).

Bacteria Lysis Buffer:

50 mM Tris buffer (pH 7.5), 4 M urea, 0.1% triton. All the chemicals mentioned were purchased from Sigma (St. Louis, Mo.).

Artificial Cerebrospinal Fluid (ACSF):

119 mM NaCl, 26.2 mM $NaHCO_3$, 2.5 mM KCl, 1 mM $NaH_2PO_4$, 1.3 mM $MgCl_2$, 10 mM glucose, gas with 5% $CO_2$/95% $O_2$ for 10-15 min, then add 2.5 mM $CaCl_2$. Filter sterilize with a 0.22-µm filter apparatus, and store at 4° C. All the chemicals mentioned were purchased from Sigma (St. Louis, Mo.).

TABLE 2 ctrA LAMP primer sequences

| Primer | Sequences (5'-3') | No. bases |
|---|---|---|
| ctrA_FIP (SEQ ID NO: 4) | CAAACACACCACGCGCATCAGAT CTGAAGCCATTGGCCGTA | 41 |
| ctrA_BIP (SEQ ID NO: 5) | TGTTCCGCTATACGCCATTGG TACTGCCATAACCTTGAGCAA | 42 |
| ctrA_F3 (SEQ ID NO: 6) | AGC(C/T)AGAGGCTTATCGCTT | 19 |
| ctrA_B3 (SEQ ID NO: 7) | ATACCGTTGGAATCTCTGCC | 20 |
| ctrA_FL (SEQ ID NO: 8) | CGATCTTGCAAACCGCCC | 18 |
| ctrA_BL (SEQ ID NO: 9) | GCAGAACGTCAGGATAAATGGA | 22 |

Microorganism Culture.

*N. meningitidis* (ATCC 13098), *S. pneumoniae* (ATCC 49619) and Hib (ATCC 33533) were obtained from American Type Culture Collection (ATCC, Rockville, Md.). *N. meningitidis* and H. influenza were grown on chocolate II agar supplemented with hemoglobin and IsoVitalex plates (BD, Sparks, MD). *S. pneumoniae* was grown in TSA II agar plates supplemented with 5% sheep blood (BD, Sparks, MD). All the microorganisms were incubated at 37° C. for 48 h in an aerobic environment with 5% $CO_2$.

Microfluidic Platform Design and Fabrication.

As shown in FIG. 1, the microfluidic device for single-plexed pathogen detection comprises three layers. The top layer is the PDMS layer used for reagent delivery, including 3 micro-channels, and an inlet reservoir. The middle layer is also a PDMS layer with 6 LAMP zones 70, 3 outlet reservoirs and micro-channels downside, which is used for LAMP reaction and detection. The bottom layer is a glass slide for support. Different LAMP zones were used for negative control (NC), positive control (PC) and *N. meningitidis* detection respectively. PC DNA and its primer mix come from the Loopamp DNA amplification kit.

A chromatography paper was cut using a laser cutter and placed inside each LAMP zones. Then the specific primers for *N. meningitidis* and PC DNA were pre-coated into the LAMP zones with paper and dried in a vacuum desiccator. Then the reaction mixture was transported from inlet to fill with the LAMP zones. After that, the inlet and outlets were sealed with Epoxy. And the amplification was performed at 63° C. on a heating film for 45 minutes.

PDMS films were produced by following standard soft lithography procedures (Xia and Whitesides, (1998) *Rev. Mater. Sci.*, 1998: 31). Briefly, the liquid PDMS base and the curing agent (Corning, N.Y.) were mixed at a weight ratio of 10:1. Then the PDMS precursor mixture was poured onto a petri dish, degassed by vacuum in the vacuum desiccator for ~30 minutes, and incubated at 60° C. for overnight. Unlike the commonly used PDMS molding, micro-channels were directly created on top of the PDMS film by using the laser cutter. Inlet reservoir in the top PDMS layer, outlet reservoirs and LAMP zones in the middle PDMS layer were drilled by using biopsy punches. By exposure in an oxidizing air plasma (Ithaca, N.Y.) for 30 s, PDMS films and the glass slide were irreversibly face-to-face sandwiched bonded.

B. Results and Discussion

PDMS/Paper Hybrid Microfluidic Devices.

Paper has high surface-to-volume ratio property and form 3D structures. This property is ideal for reagents bounding to the surface of paper and benefit for assays (Martinez, (2011) *Bioanalysis*, 3:2589-92). In this work, chromatography paper was placed in the LAMP zones to form a PDMS/paper hybrid microfluidic device, serving as the substrate for adsorbing the primer in subsequent steps. And primer was absorbed and stored in the LAMP zones with paper uniformly even when they are dry, as we can see from the microscope image (FIG. 6) taking by a high-resolution fluorescence microscope (Ti-E, Nikon, NY) at the same exposure time. On the contrary, for the LAMP zones without paper, primer accumulated on the edge of the circle of LAMP zones when they are dry.

Figures 2A, 2B, 2C, 2D:
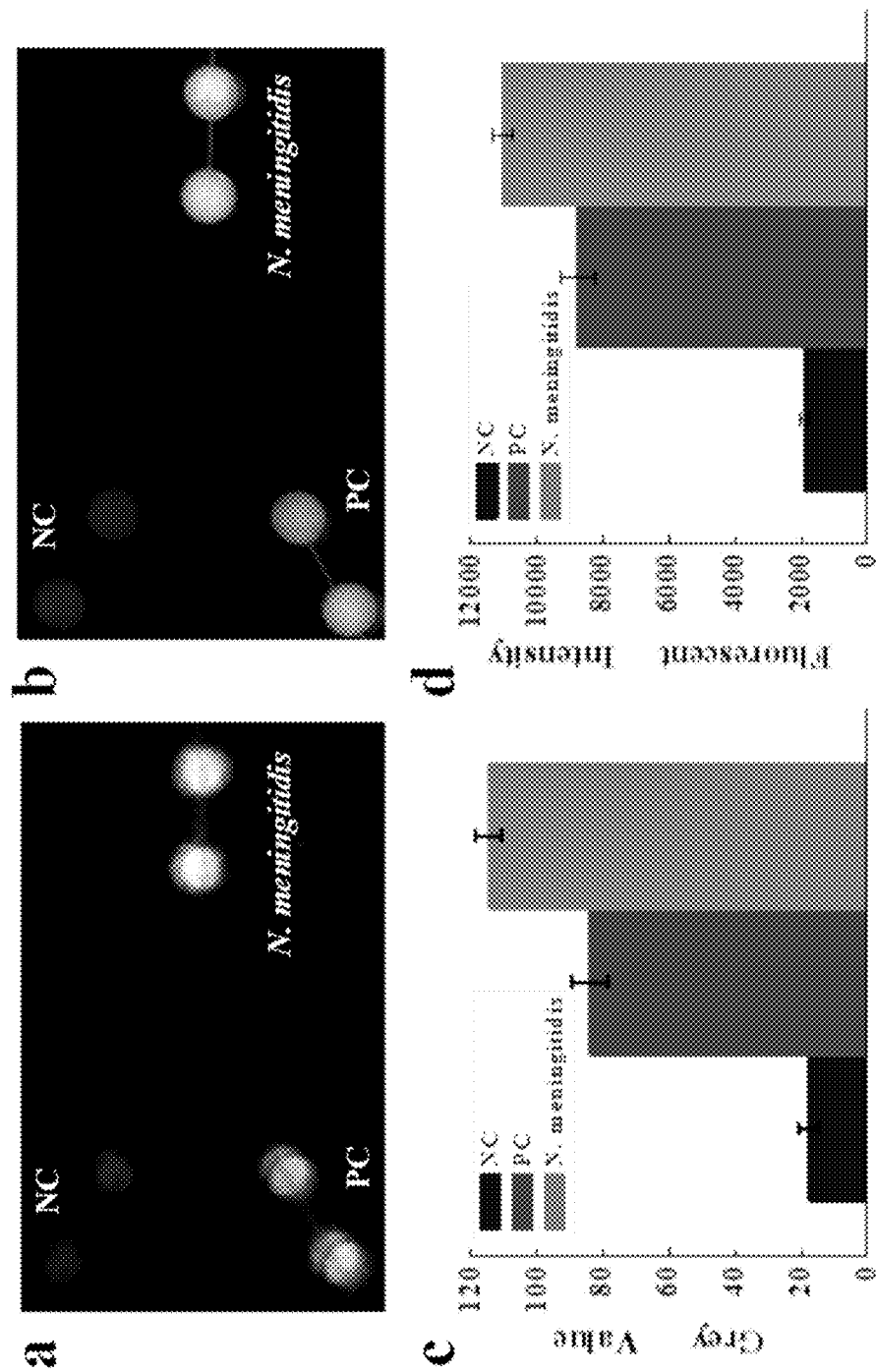
FIG. 2A-2D. On-chip LAMP detection of $N$ meningitidis using purified DNA by a portable UV light pen (a) and fluorescence microscopy (b). Strong fluorescence was observed in $N.$ meningitidis and PC LAMP zones, but not in NC zones. (c) Gray value of the LAMP products measured by ImageJ; (d) Fluorescent intensity of the LAMP products measured by fluorescence microscope. The purified DNA template used was $3\times10^6$ copies per LAMP zone.
Figures 6A, 6B, 6C:
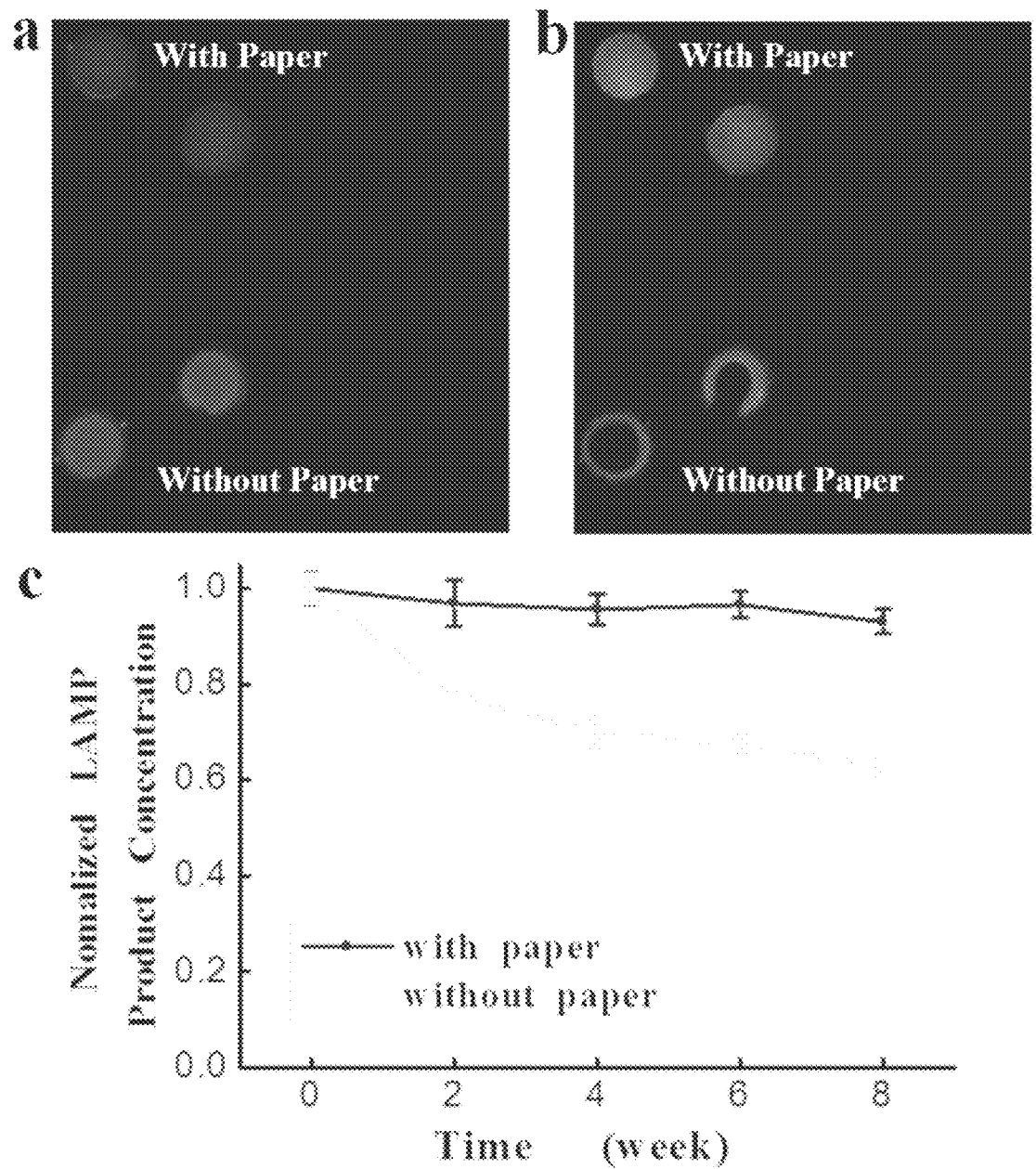
FIG. 6A-6C. (a-b) Fluorescence images of pre-loaded Cy3-labelled primers in LAMP zones either with or without paper inside. When LAMP zones were dry, primers in paper-free LAMP zones accumulated on the edge of the LAMP zones, while primers in LAMP zones with paper inside were still uniformly distributed. (c) On-chip LAMP performance comparison between biochips with paper inside and without paper inside over a period of two months. Nucleic acid concentration of *N. meningitidis* LAMP products from LAMP zones with paper inside and without paper inside was measured to evaluate on-chip LAMP performance between these two different kinds of biochips. DNA concentration was normalized for convenient comparison.

In addition, dried paper is believed to be able to protect DNA in harsh conditions, and is commonly used to collect forensic samples (Smith and Burgoyne, (2004) *BMC Ecology*, 4(1): 4; Chaisomchit et al. (2005) *Southeast Asian J Trop Med Public Health*, 36(1): 270-273). Therefore, we believe the paper inside a ready-to-use devices can protect DNA primers, thus enabling stable results over a long period of time and long shelf life of the device, as shown in FIG. 6C. We investigated and compared the on-chip LAMP performance of the devices with paper inside and without paper inside over a period of two months at room temperature. We pre-coated LAMP primers of *N. meningitidis* in LAMP zones with paper inside or without paper inside. The two kinds of ready-to-use microfluidic chips were stored at the same conditions in dark. LAMP reactions were performed within 2 weeks, 4 weeks, 6 weeks and 8 weeks, respectively. LAMP products were quantified by using Nanodrop after each LAMP reaction to evaluate the on-chip LAMP performance. As shown in FIG. 2c, the nucleic acid concentration of LAMP product from LAMP zones without paper inside kept decreasing through the whole experimental period. A sharp decrease within the first two weeks was observed. At week 8, the on-chip LAMP performance decreased by ~40%, which implied that the devices without paper inside were not able to provide consistent results over a period of time. Such devices without paper inside needed to be used right away. On the contrary, the on-chip LAMP performance from the device with paper inside maintained stable within two months. Only slight decrease (less than 6%) over time was observed. Therefore, we concluded that the introduction of paper in this hybrid microfluidic biochip as a primer storage substrate also enabled stable on-chip LAMP performance and longer shelf life than those without paper inside.

*N. meningitidis* Detection Using Purified DNA.

The feasibility of the PDMS/paper hybrid microfluidic platform for *N. meningitidis* detection was tested by using purified DNA. The *N. meningitidis* DNA template was obtained from bacterial culture and DNA isolation. By using this DNA template, we carried out the LAMP on chip. 25.5 µL LAMP reaction mix were transported, including the PC DNA, through the inlet reservoir into the LAMP zones, where the specific LAMP primers for the target *N. meningitidis* and PC DNA sequences have been precoated (no primer was pre-coated in the LAMP zones for NC). After the inlet and outlets reservoirs were sealed, the microfluidic device was placed on a heating film at 63° C. for 45 minutes for LAMP reaction. A notable feature of the device design is that the channels in the middle PDMS layer were independent without connections, so that this could effectively prevent cross-talk among the LAMP zones with different purposes (NC, PC and *N. meningitidis* detection) from each other during the LAMP reaction.

Figures 3A, 3B, 3C, 3D, 3E:
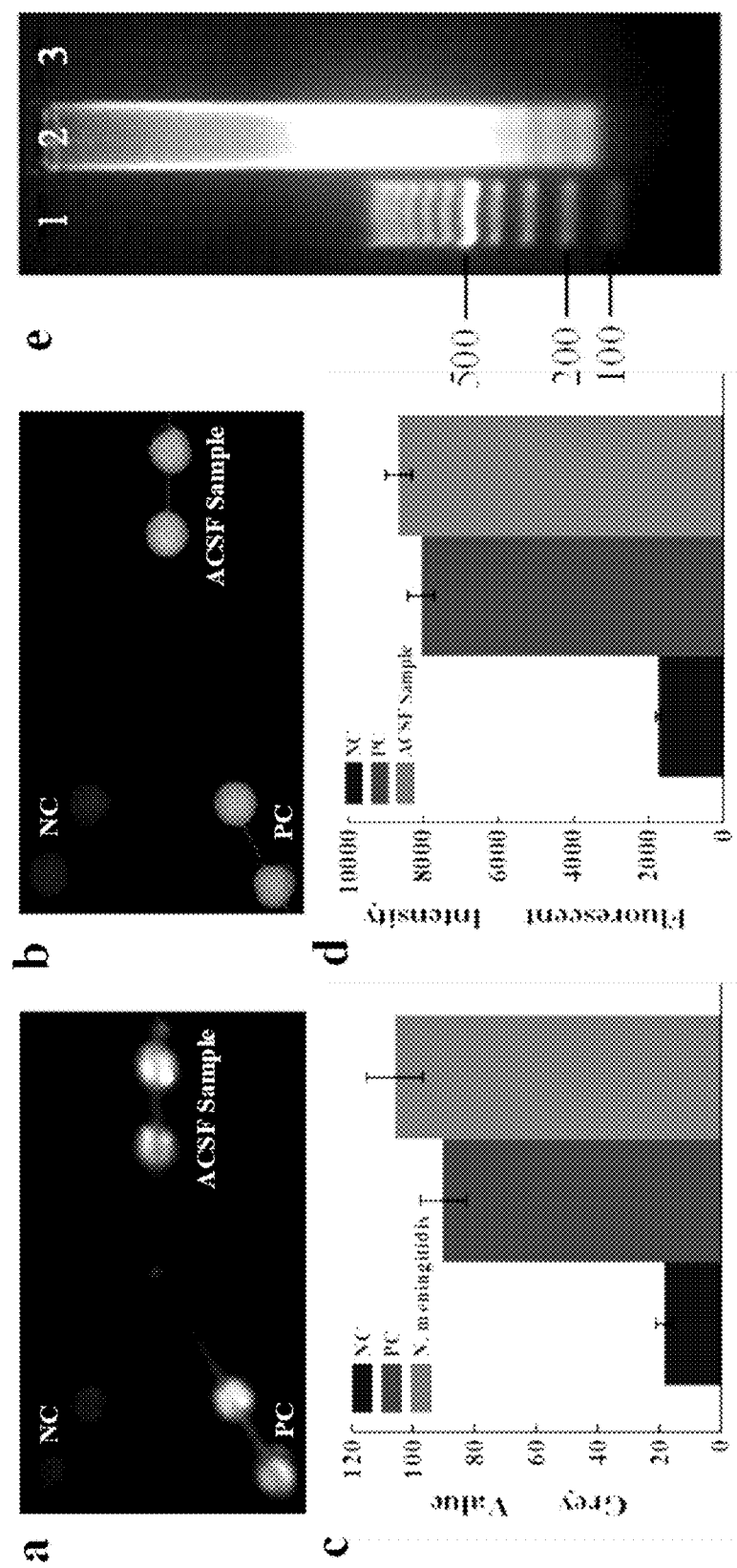
FIG. 3A-3E. Instrument-free detection of $N.$ meningitidis microorganisms. Fluorescence images of on-chip LAMP detection of $N.$ meningitidis in ACSF under portable UV light (a) and by fluorescence microscopy (b). (c) Gray value of the LAMP products from pathogen/ACSF mixtures measured by fluorescence microscope. (d) Fluorescent intensity of the LAMP products from pathogen/ACSF mixtures measured by fluorescence microscope. (e) Gel electrophoresis of the on-chip LAMP products of *N. meningitidis* in ACSF. Lanes 1-3: 100 bp marker; LAMP products of *N. meningitidis* in ACSF; NC.

Before LAMP, the fluorescence detection reagent calcein is quenched by manganese ion. After LAMP, the reaction by product pyrophosphate ions form a complex with manganese. And the free calcein combines with a magnesium ion to produce bright fluorescence. Therefore, the detection result could be directly determined by eyes based on the fluorescence of the LAMP zones under portable UV light. Results showed that *N. meningitidis* and PC exhibited bright green fluorescence under portable UV light after the LAMP reaction, NC did not, which could be seen from the picture (FIG. 2a). This was consistent with the averaged grey value of the picture measured by ImageJ software (FIG. 2b), which is used to indicate the 70 brightness of a pixel. And here the averaged grey value was indicators for fluorescence intensities. The fluorescent intensity was further measured by the fluorescence microscope directly (FIG. 3b and FIG. 3d). The fluorescence intensity of the *N. meningitidis* LAMP products was about 6 times more than that of the NC.

In addition, cured Epoxy could be uncovered after heating, and the LAMP products could be collected from each outlet for further analysis. The obvious difference could be seen even by naked eyes after collecting the LAMP products into small tubes, which were used for further gel electrophoresis to confirm the result. Results show that the *N. meningitidis* LAMP products exhibited very bright fluorescent while the NC mixture had no difference after LAMP reaction. As expected, the ladder pattern bands of the *N. meningitidis* products verified the success of the on chip LAMP.

Direct Pathogen Detection on a PDMS/Paper Hybrid Microfluidic Platform.

There have been reports on direct and rapid PCR detection for clinic samples or pathogenic bacteria by using special lysis reagent without inhibition (Liu et al. (2011), *Lab on a Chip*, 11: 1041-48; Burr et al. (2001), *Plant Mol Biol Rep*, 19: 367-71; Vickers et al. (2011) *Eur J Clin Microbiol Infect Dis*, 30: 447-53; Ke et al. (2007) *Sensors and Actuators B: Chemical*, 120: 538-44). But for LAMP reaction, traditional sample preparation procedures such as DNA isolation and purification are needed, which consume a lot of time and have a risk of contamination. According to a report, LAMP on chip for identifying bacteria directly was achieved by using bacterial lysis buffer and heating (~80° C.) for DNA release from bacterium (Fang et al. (2012) *Lab on a Chip*, 12: 1495-99). However, it had a strict requirement for sealing of the "DNA release chamber" to generate enough vapor pressure to pump out the bacteria/lysis buffer mixture, and even though the recovery was still very low (~1 μL liquid was obtained from ~10 μL mixture).

The inventors carried out direct pathogen detection, which integrated the bacteria lysis procedure with on chip LAMP reaction with simple and easy sample preparations. Instead of using isolated DNA template, artificial cerebrospinal fluid (ACSF)/pathogen mixture was prepared to mimic the real clinic samples for on chip LAMP reaction. Details were as follows: First, colony from cultured plates was swabbed by using an inoculation loop and mixed with 20 μL ACSF buffer to prepare the ACSF/pathogen mixture. A tiny amount should be enough as it was just visible to the eyes (avoiding agar contamination). Then 2 μL of this mixture was added into 18 μL bacterial lysis buffer, and incubated at room temperature for about 10 minutes. At last, 2 μL of the ACSF/pathogen mixture lysate was used in LAMP reaction mixture (same amount as using DNA template) for LAMP reaction. The results showed that the LAMP products of the ACSF sample could still produce strong fluorescence as previously (FIG. 3a-3d). And gel electrophoresis confirmed the success of the LAMP reaction (FIG. 3e). The direct pathogen detection was very significant because it indicated that real samples could be directly used for the on chip LAMP reaction without any laborious and time-consuming DNA isolation or purification pretreatment in advance.

Calibration Curve for N. meningitidis.

Figure 4:
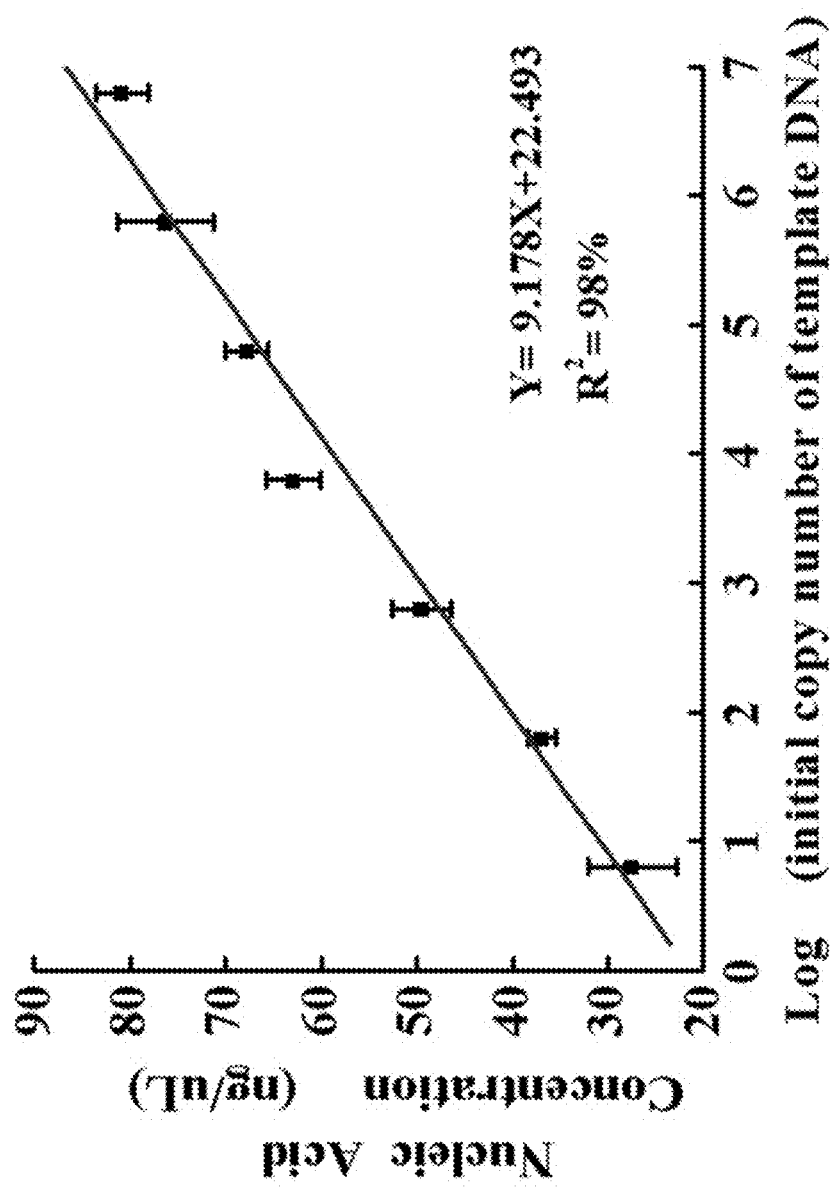
FIG. 4. Calibration curve of nucleic acid concentration of the LAMP products (after LAMP amplification) versus the initial copy number of template DNA (before LAMP amplification) of *N. meningitidis* in ACSF.

The visual fluorescence detection was a rapid and direct method for end-point LAMP pathogen detection, from which a yes or no qualitative answer for point of care (POC) detection was achieved based on the fluorescence of the LAMP products. However, it cannot achieve quantitative results. By using the versatile microfluidic platform, quantitative analysis was achieved by collecting LAMP products for further simple off-chip treatment. In brief, a serial of 10 fold diluted ACSF/pathogen mixture lysate were prepared for LAMP reaction, the nucleic acid concentration of which was measured by Nanodrop to get the initial copy number of released DNA based on one LAMP zone. After the LAMP reaction, LAMP products collected, purified, and measured for nucleic acid concentration by Nanodrop to obtain a calibration curve (FIG. 4). The result showed the nucleic acid concentration increased in proportion to the initial copy number of template DNA. Therefore, by measuring the nucleic acid concentration of the LAMP products from samples, one can infer the amount of the initial bacteria and how serious the infection is.

Limit of Detection (LOD) for N. meningitidis.

Figures 5A, 5B, 5C:
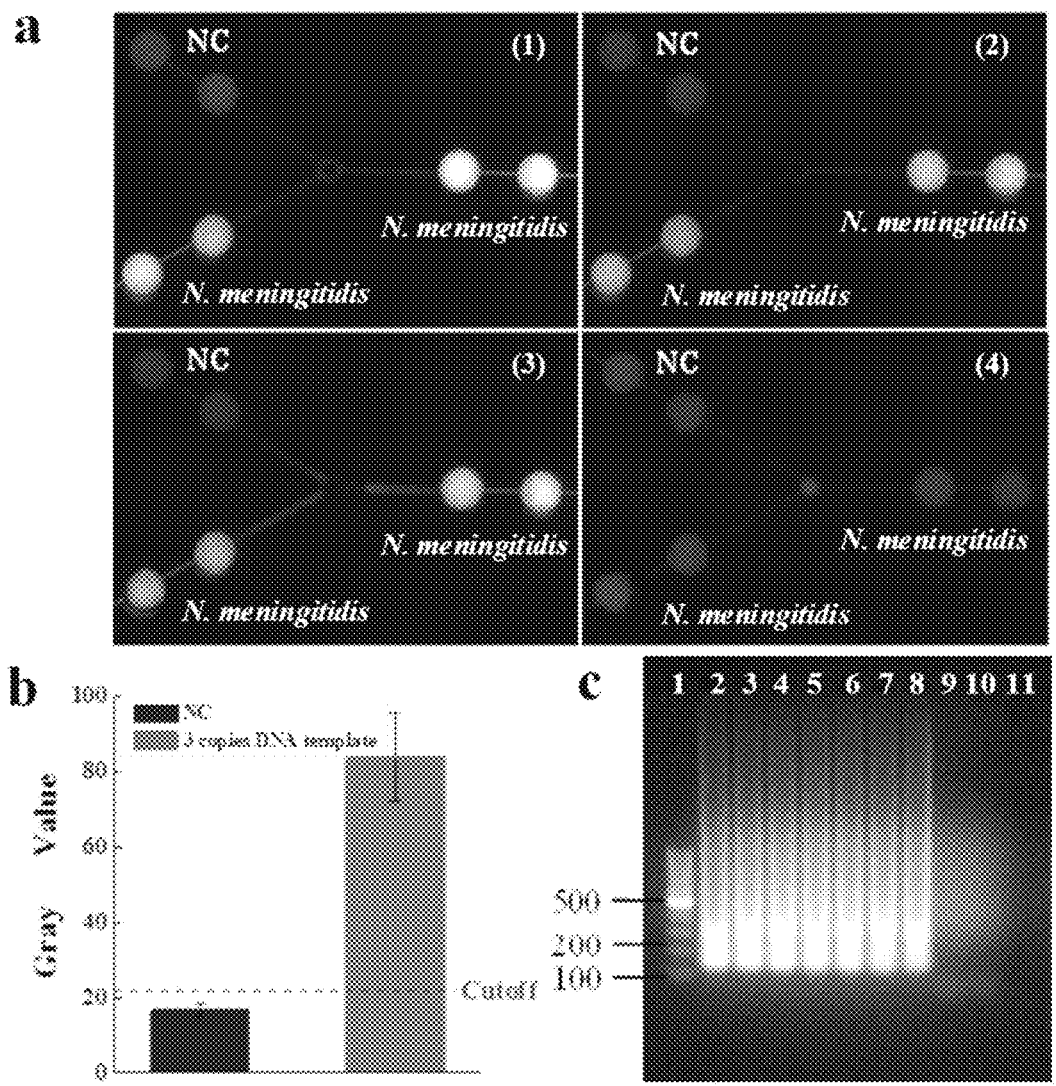
FIG. 5A-5C. LOD investigation. (a) Fluorescence images of LAMP products using a series of 10 fold diluted *N. meningitidis* DNA template solutions ranging from (1)-(4): $3 \times 10^2$, $3 \times 10^1$, $3 \times 10^0$, $3 \times 10^{-1}$ DNA copies per LAMP zone. The on-chip LAMP products still exhibited strong fluorescence even the initial DNA templates were as low as 3 copies per LAMP zone. (b) Gray values of the image of (a)-3 for LAMP products from 3 copies DNA template. The dotted line is the calculated gray value of the cutoff line for *N. meningitidis* detection based on 3 times SD of negative controls. (c) Gel electrophoresis of on-chip LAMP products using a series of diluted DNA template solutions. Lanes 1-11: 100 bp marker, $3 \times 10^6$, $3 \times 10^5$, $3 \times 10^4$, . . . , $3 \times 10^0$, $3 \times 10^{-1}$, $3 \times 10^{-2}$ DNA copies of the template per LAMP zone, NC.

By using a serial of 10 fold diluted initial copy number of DNA template, the limit of detection was tested. The top left LAMP zones of the device were used for NC. The other LAMP zones were used for N. meningitidis DNA detection. The LOD of N. meningitidis was 3 copies per LAMP zone. This was identical when measured by fluorescent intensity, direct visual inspection or gel electrophoresis. The results showed that even the initial DNA template were as low as 3 copies per LAMP zone, the on chip LAMP products still exhibited strong fluorescence. However, when the initial DNA template was less than one copy, the fluorescence of the LAMP zones was as dim as the NC (FIG. 5). The gel electrophoresis confirmed the result (FIG. 5c). The band of the LAMP products with initial DNA template at or more than 3 copies indicated the success of the on chip LAMP reaction. FIG. 5c shows gel electrophoresis of on-chip LAMP products with a serial of diluted initial copy number of template DNA. Lanes 1-11: 100 bp marker; $3\times10^6$; $3\times10^5$, $3\times10^4$, . . . , $3\times10^0$, $3\times10^{-1}$, $3\times10^{-2}$ initial copies of template DNA per LAMP zone, NC.

The inventors have developed a versatile PDMS/paper hybrid microfluidic platform for rapid and sensitive detection of N. meningitidis. Due to the integrated LAMP DNA amplification on the chip, the limit of detection of ~3 DNA copies of N. meningitidis has been achieved within 45 minutes, overcoming lengthy assay time and low-sensitivity issues in conventional methods for the diagnosis of meningitis. This hybrid microfluidic platform incorporates the advantages of high performance in liquid control from PDMS and of high porosity from paper for pre-loading LAMP primers.

The function of this hybrid microfluidic system is versatile. (1) Its on-chip LAMP detection based on calcein under portable UV light doesn't require any bulky specialized equipment without the use of any centrifuges and cumbersome procedures for DNA isolation and purification. The instrument-free detection makes the microfluidic system highly capable for the diagnosis of meningitis in the field or in other resource-limited settings. (2) The design of the microfluidic biochip allows on-chip LAMP products to be readily extracted for more confirmatory tests (e.g. gel electrophoresis) and quantitative analysis based on the calibration curve, as demonstrated in this work. This feature is suitable to the in-depth analysis and study of patient samples in clinical laboratory settings. Combining features (1) and (2) can provide a comprehensive examination of patient samples in different settings. For instance, after an initial qualitative assay of a patient sample in the field or resource-limited settings, the sample tested by the biochip can be sent back to a clinical laboratory for further confirmatory tests or quantitative analysis to examine the disease seriousness of infection. Moreover, by designing and changing different primers specific to other infectious diseases, this microfluidic platform can have great potential in quick and early diagnosis of a broad range of other infectious diseases, such as, whooping cough, malaria, H1N1, and severe acute respiratory syndrome (SARS), especially for developing nations.

Example 2

Multiplexed Detection

Figures 7A, 7B:
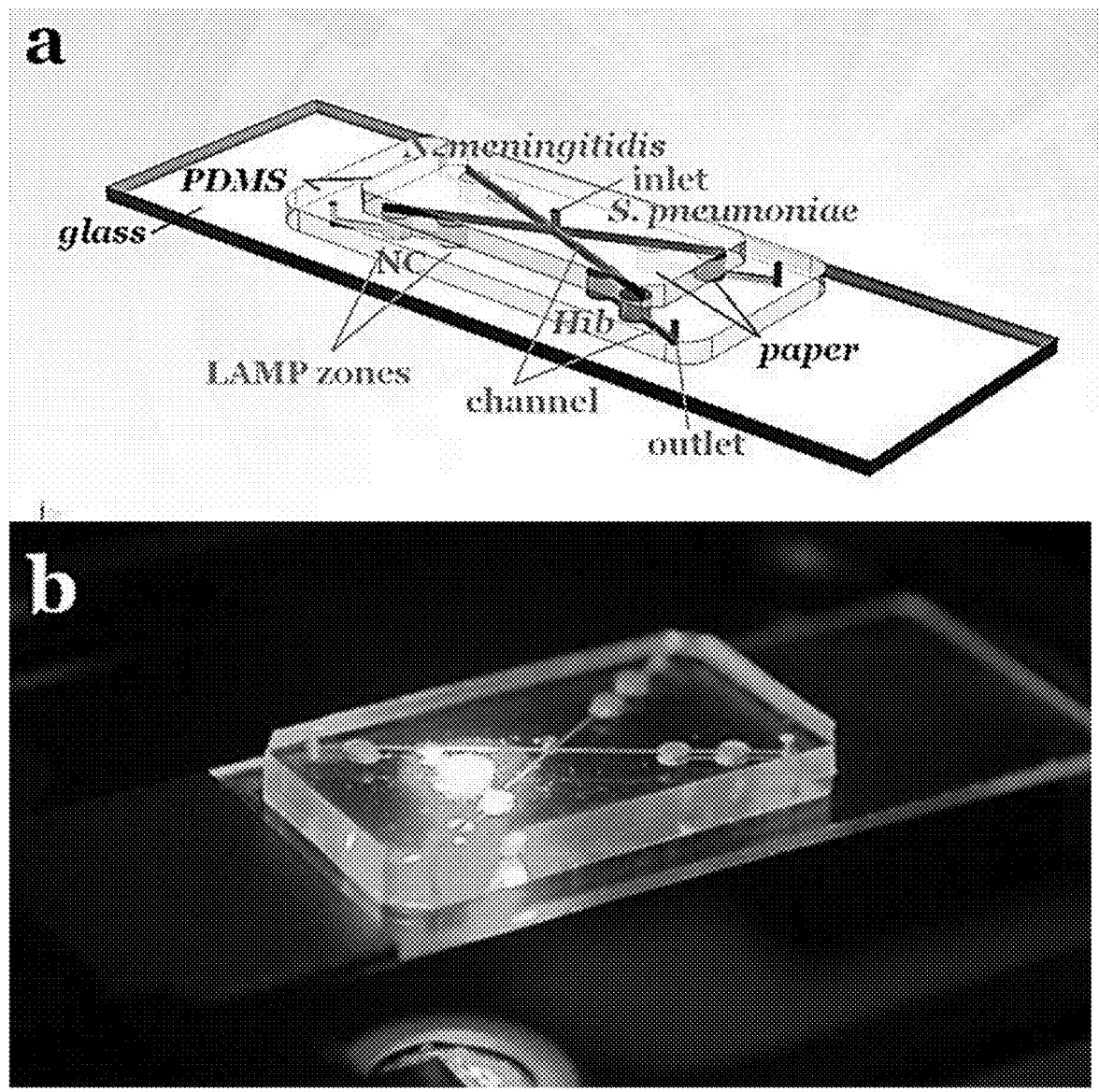
FIG. 7A-7B. Chip layout of the PDMS/paper hybrid microfluidic device for multiplexed instrument-free pathogen detection. (a) 3D illustration of the schematic of the chip layout. The chip consists of one top PDMS layer, one middle PDMS layer and one glass slides for reagent delivery, LAMP reaction and structure support, respectively. A chromatography paper disk is situated inside each LAMP zone to preload LAMP primers. (b) A photograph of the hybrid microfluidic device for multiplexed bacterial meningitis diagnosis.

As shown in FIG. 7, by increasing the number of channels on the top layer and corresponding LAMP wells in the middle layer, the microfluidic device is capable of multiplexed detection. Herein, simultaneous detection of N. meningitidis, S. pneumoniae detection and Hib is just one of such examples. However, the channels and LAMP zones can be further scaled up for simultaneous detection of more different types of pathogens.

Direct Pathogenic Microorganisms Detection by Using ACSF Samples.

Similar to Example I, the pathogen detections were first tested by using purified DNA. However, real clinical samples are usually from cerebrospinal fluid (CSF) or blood, which need special treatment for pathogen lysis and DNA release for DNA amplification. Traditional clinical sample preparation procedures such as DNA isolation and purification not only consume a lot of time, rely on specialized equipment in laboratories, but also increase the risk of contamination, which are not applicable for point of care pathogen detection.

Figures 8A, 8B, 8C, 8D, 8E:
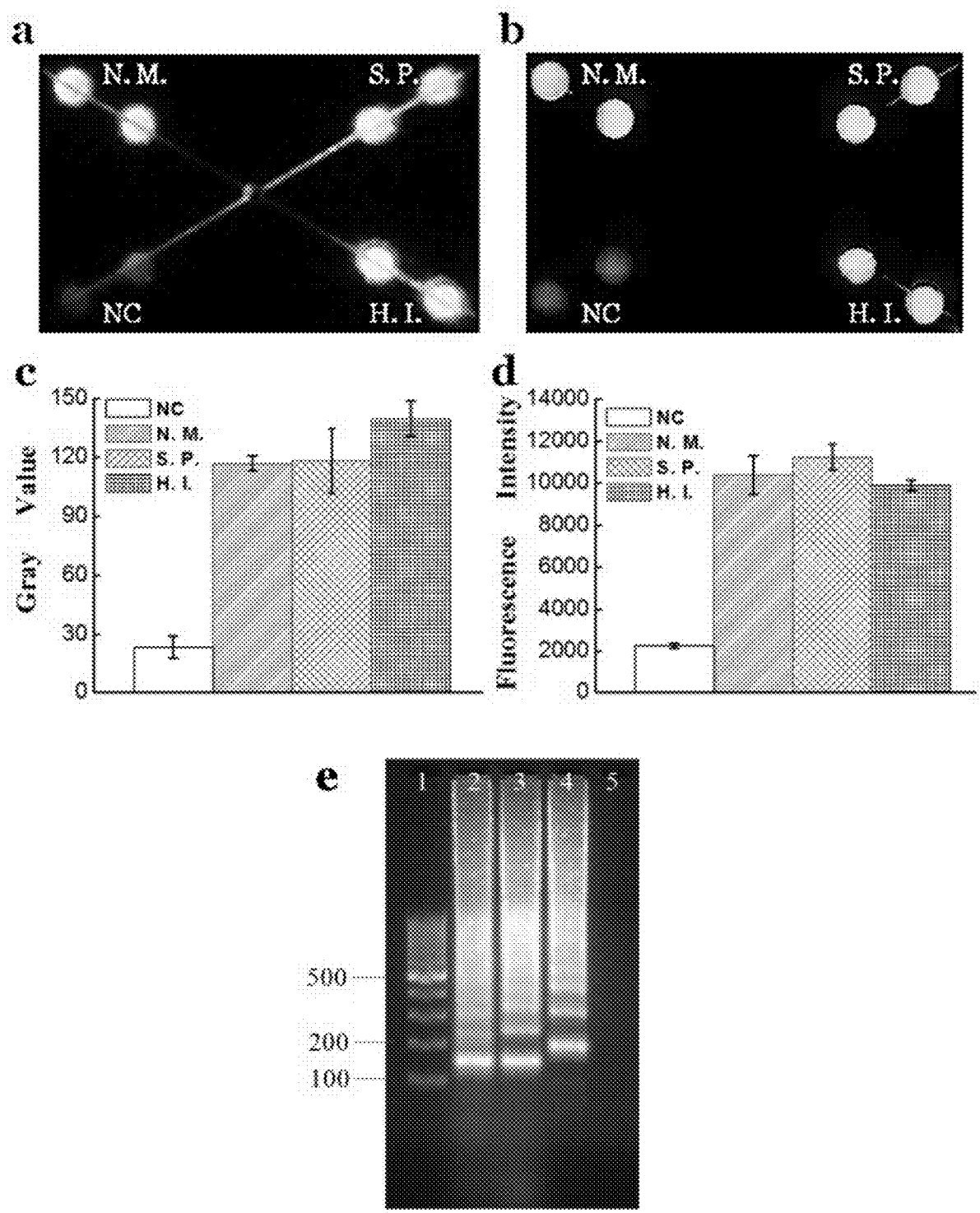
FIG. 8A-8E. On-chip LAMP multiplexed pathogen detection of *N. meningitidis, S. pneumoniae* and Hib using purified DNA by a portable UV light pen (a) and fluorescence microscopy (b). Strong fluorescence was observed in sample detection zones, but not in NC zones. (c) Gray value of the LAMP products measured by ImageJ; (d) Fluorescent intensity of the LAMP products measured by fluorescence microscope. (e) Gel electrophoresis of collected LAMP product for confirmatory analysis. Lanes 1-5: 100 bp ladder, LMAP product from *N. meningitidis, S. pneumoniae* and Hib, NC. Ladder-pattern DNA bands were observed in LMAP products from sample detection zones, whereas no DNA bands were observed in NC. The purified DNA template of *N. meningitidis, S. pneumoniae* and Hib used was $3 \times 10^6$, $6 \times 10^6$ and $5 \times 10^6$, copies per LAMP zone.

In this work, we developed a direct pathogen detection approach with simple and easy sample preparation. To mimic the real clinical samples, we prepared artificial cerebrospinal fluid (ACSF) samples with pathogenic microorganisms contained for microfluidic chip LAMP reaction and detection. As shown in FIGS. 8a and 8b, LAMP product from the three pathogens by using ACSF sample produced bright fluorescence under a portable UV light pen and fluorescent microscope, with the gray value and fluorescence intensity indicated in FIGS. 8c and 8d. Gel electrophoresis of LAMP product from the three pathogens showed the ladder-pattern bands (FIG. 8e), confirming the success of the microfluidic on-chip LAMP for simultaneous detection of these three pathogen.

Similarly, the quantitation of the three pathogens can be performed using the indirect approach we developed in Example I.

Limit of Detection (LOD).

Figures 9A, 9B, 9C, 9D:
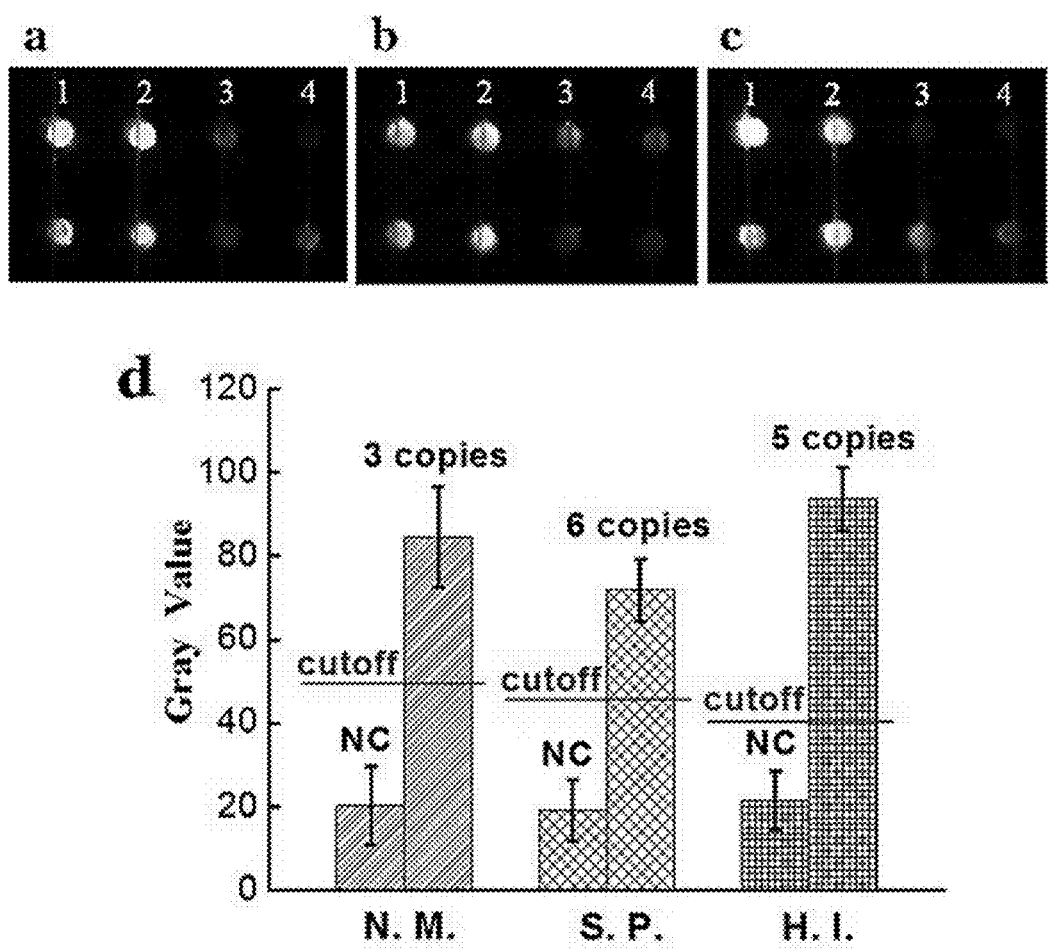
FIG. 9A-9D. LOD investigation by a portable UV light pen and gray values. (a) Detection of *N. meningitidis* by a portable UV light pen using a series of 10 fold diluted *N. meningitidis* DNA template solutions ranging from (1)-(4): $3 \times 10^1$, $3 \times 10^0$, $3 \times 10^{-1}$ DNA copies per LAMP zone, NC. (b) Detection of *S. pneumoniae* by a portable UV light pen using a series of 10 fold diluted *S. pneumoniae* DNA template solutions ranging from (1)-(4): $6 \times 10^1$, $6 \times 10^0$, $6 \times 10^{-1}$ DNA copies per LAMP zone, NC. (c) Detection of Hib by a portable UV light pen using a series of 10 fold diluted Hib DNA template solutions ranging from (1)-(4): $5 \times 10^1$, $5 \times 10^0$, $5 \times 10^{-1}$ DNA copies per LAMP zone, NC. (d) Gray values of the images of (a)-2, (b)-2, and (c)-2 for LAMP product from 3 copies *N. meningitidis* (N. M.) DNA template, 6 copies *S. pneumoniae* (S. P.) DNA template and 5 copies Hib (H. I.) DNA template as well as their corresponding NC respectively. The dash line was the cutoff gray value for its corresponding pathogen's LOD.

By using a serial of 10 fold diluted initial copy number of template DNA, the limit of detection for each pathogen was tested. The LOD of N. meningitidis, S. pneumoniae and Hib was 3 copies, 6 copies and 5 copies per LAMP zone, respectively. This was identical when measured by gray value, fluorescent intensity or gel electrophoresis. Results (FIG. 9) indicated that even when the initial template DNA was as low as a few copies per LAMP zone, LAMP products still exhibited strong fluorescence. However, when the initial template DNA was less than one copy, the fluorescence of the LAMP zones was not lit up. Based on 3 fold standard deviations of the mean gray value of the negative controls on the basis of the negative control, the gray value of the cutoff line for N. meningitidis, S. pneumoniae and Hib was calculated, which was 48.1, 41.3 and 42.5 respectively. The gray value of the LAMP product from 3 copies of initial DNA template of N. meningitidis, 6 copies of initial DNA template of S. pneumoniae and 5 copies of initial DNA template of Hib was much higher than that of cutoff line. Gel electrophoresis confirmed the result.

The invention claimed is:

1. A biochip for pathogen detection comprising a polymer/paper hybrid microfluidic device comprising at least four separate layers, wherein the at least four separate layers comprise:

a top polymer layer comprising an inlet reservoir and microchannels connected to the inlet reservoir;

a middle paper layer positioned below the top polymer layer, said middle paper layer comprising:

(a) an amplification layer having at least one cylindrical amplification well forming a cylindrical hole in the amplification layer having an open top portion being in fluid communication with the inlet reservoir of the top layer, a closed bottom portion positioned 1 millimeter (mm) to 4 mm below the top layer, and a horizontal cross-sectional diameter 0.5 mm to 3 mm, the at least one amplification well is configured to receive an amplification mixture and perform a nucleic acid amplification reaction during use to produce an amplified product;

(b) a detection layer in fluid communication with the amplification layer, the detection layer comprising at least one cylindrical detection well forming a cylindrical hole in the detection layer having a top portion and a closed bottom portion positioned 1 mm to 4 mm below the top layer, and a horizontal cross-sectional diameter 0.5 mm to 3 mm, said at least one detection well is in fluid communication with the at least one amplification well and is configured to receive an amplified product from the amplification well during use;

a paper insert layer comprising an absorbed detection reagent, said paper insert layer having a thickness of 0.05 to 0.25 mm and a pore diameter of 5 micrometers (μm) to 15 μm and is positioned inside the at least one detection well and is disposed directly on the closed bottom part of the at least one cylindrical detection well, said paper insert layer forms a separate layer within the cylindrical detection well and is thinner than the detection layer; and a polymer or glass support layer positioned below the detection layer, wherein the top polymer layer, the middle paper layer, the paper insert layer and the polymer or glass support layer form the at least four separate layers of the polymer/paper hybrid microfluidic device.

2. The biochip of claim 1, wherein the polymer/paper hybrid microfluidic device comprises a plurality of amplification wells.

3. The biochip of claim 1, wherein the polymer is polydimethysiloxane (PDMS).

4. The biochip of claim 1, wherein the absorbed detection reagent on the paper insert layer comprises DNA primers.

5. The biochip of claim 1, wherein the polymer or glass support layer is glass.

6. The biochip of claim 1, wherein the amplification layer further comprises multiple sublayers.

7. The biochip of claim 6, wherein the multiple sublayers are cut to form amplification wells.

8. The biochip of claim 1, wherein the detection layer comprises the at least one cylindrical detection well linked to reagent delivery channels.

9. The biochip of claim 1, further comprising a sequence specific probe in the at least one cylindrical detection well.

10. The biochip of claim 1, wherein the top polymer layer further comprises a filter configured to remove components of a sample and to provide a filtered sample to the at least one cylindrical amplification well.

* * * * *

SEQUENCE LISTING

```
<160> NUMBER OF SEQ ID NOS: 9

<210> SEQ ID NO 1
<211> LENGTH: 32
<212> TYPE: DNA
<213> ORGANISM: Neisseria meningitidis

<400> SEQUENCE: 1
aaccttgagc aatccattta tcctgacgtt ct                                   32

<210> SEQ ID NO 2
<211> LENGTH: 28
<212> TYPE: DNA
<213> ORGANISM: Haemophilus influenzae

<400> SEQUENCE: 2
gcggattccc agttgagtgt gcgtgtac                                        28

<210> SEQ ID NO 3
<211> LENGTH: 23
<212> TYPE: DNA
<213> ORGANISM: Streptococcus pneumoniae

<400> SEQUENCE: 3
tggtgctaag atgaagttat ggc                                             23

<210> SEQ ID NO 4
<211> LENGTH: 41
<212> TYPE: DNA
<213> ORGANISM: Artificial Sequence
<220> FEATURE:
<223> OTHER INFORMATION: Synthetic Primer

<400> SEQUENCE: 4
caaacacacc acgcgcatca gatctgaagc cattggccgt a                         41

<210> SEQ ID NO 5
<211> LENGTH: 42
<212> TYPE: DNA
<213> ORGANISM: Artificial Sequence
<220> FEATURE:
<223> OTHER INFORMATION: Synthetic Primer

<400> SEQUENCE: 5
```

```
tgttccgcta tacgccattg gtactgccat aaccttgagc aa                           42

<210> SEQ ID NO 6
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(4)
<223> OTHER INFORMATION: N is C or T

<400> SEQUENCE: 6
agcnagaggc ttatcgctt                                                    19

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
ataccgttgg aatctctgcc                                                   20

<210> SEQ ID NO 8
<211> LENGTH: 18
<212> TYPE: DNA
<213> ORGANISM: Artificial Sequence
<220> FEATURE:
<223> OTHER INFORMATION: Synthetic Primer

<400> SEQUENCE: 8
cgatcttgca aaccgccc                                                     18

<210> SEQ ID NO 9
<211> LENGTH: 22
<212> TYPE: DNA
<213> ORGANISM: Artificial Sequence
<220> FEATURE:
<223> OTHER INFORMATION: Synthetic Primer

<400> SEQUENCE: 9
gcagaacgtc aggataaatg ga                                                22
```